United States Patent [19]
Curtze et al.

[11] Patent Number: 5,773,663
[45] Date of Patent: Jun. 30, 1998

[54] FUNGICIDAL METHODS, COMPOUNDS AND COMPOSITIONS CONTAINING BENZOPHENONES

[75] Inventors: Jurgen Curtze, Geisenheim; Christine Helene Gertrud Rudolph, Nierstein; Ludwig Schroder, Ingelheim; Guido Albert, Hackensheim; Annerose Edith Elise Rehnig, Ingelheim; Ewald Gerhard Sieverding, St. Johann, all of Germany

[73] Assignee: American Cyanamid Company, parsippany, N.J.

[21] Appl. No.: 641,592

[22] Filed: May 1, 1996

[51] Int. Cl.⁶ .......................... C07C 49/24; A61K 31/12
[52] U.S. Cl. .............................. 568/333; 514/687
[58] Field of Search ............... 568/333; 514/687

[56]   References Cited

U.S. PATENT DOCUMENTS

| | | | |
|---|---|---|---|
| 3,560,567 | 2/1971 | Ruegg et al. | 568/333 |
| 3,924,002 | 12/1975 | Duennenberger et al. | 568/333 |
| 3,983,176 | 9/1976 | Yamada et al. | 568/333 |
| 4,124,726 | 11/1978 | Hamazaki et al. | 568/222 |
| 4,329,360 | 5/1982 | Resnick | 568/333 |
| 4,530,844 | 7/1985 | Smerbeck et al. | 568/333 |
| 4,801,616 | 1/1989 | Gapinski | 568/333 |

*Primary Examiner*—James H. Reamer
*Attorney, Agent, or Firm*—Gregory M. Hill

[57]   ABSTRACT

There is provided a method for the control of phytopathogenic fungi and disease caused thereby which comprises contacting said fungi with a fungicidally effective amount of a benzophenone compound of formula I

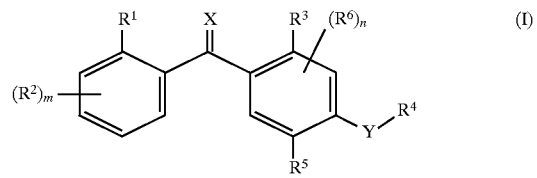

There are further provided benzophenone compounds of formula Ia which are useful as fungicidal agents and compositions useful for the protection of plants from the damaging effects of phytopathogenic fungi and fungal disease.

2 Claims, No Drawings

FUNGICIDAL METHODS, COMPOUNDS AND COMPOSITIONS CONTAINING BENZOPHENONES

BACKGROUND OF THE INVENTION

Food production relies upon a variety of agricultural technologies to ensure the growing population's dietary needs remain affordable, nutritious and readily available on grocery store shelves. Fungicides are one of these agricultural technologies which are available to the world community. Fungicides are agrochemical compounds which shield crops and foods from fungus and fungal diseases. Crops and food are constantly threatened by a variety of fungal organisms, which, if left uncontrolled, can cause ruined crops and devastated harvests.

In particular, ascomycetes, the causative agent for powdery mildew diseases are an ever-present threat especially to cereal and fruit crops. However, applications of fungicidal agents at disease control rates can cause phytotoxic damage to the target plants.

Therefore it is an object of this invention to provide a method to control phytopathogenic fungus without causing concurrent phytotoxic damage to the host plant.

It is another object of this invention to provide an effective and safe method for the protection of important agronomic crops from the damage and loss caused by a phytopathogenic fungal infection and the disease caused thereby.

It is a further object of this invention to provide benzophenone fungicidal agents and fungicidal compositions comprising a benzophenone compound.

These and other objects and features of the invention will become apparent from the detailed description provided hereinbelow.

SUMMARY OF THE INVENTION

The present invention provides a method for the control of a phytopathogenic fungus or a disease caused thereby which comprises contacting said fungus with a fungicidally effective amount of a benzophenone compound of formula I

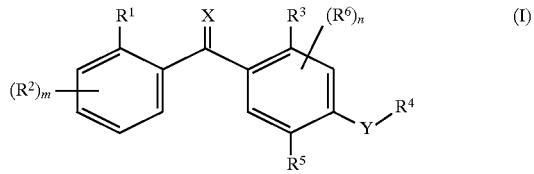

wherein $R^1$ represents a halogen atom, an optionally substituted alkyl or alkoxy group, a cyano or a nitro group; m is 0 or an integer of 1, 2, 3 or 4; $R^2$ independently represents a halogen atom, an optionally substituted alkyl or alkoxy group, a nitro group or when $R^1$ and $R^2$ are attached to adjacent carbon atoms, $R^1$ and one $R^2$ may be taken together to represent —CH=CH—CH=CH— or optionally substituted alkylene or oxyalkyleneoxy, such as O—$CF_2$—O; $R^3$ represents hydrogen, halogen, an optionally substituted alkyl, alkoxy, alkenyl, alkylthio, alkylsulphinyl, alkylsulphonyl, cyano, carboxy, hydroxy, nitro, or an optionally substituted amino group; $R^4$ represents a hydrogen atom or an optionally substituted alkyl or acyl group; $R^5$ represents a hydrogen, halogen, an optionally substituted alkyl, alkoxy, alkenyloxy, alkynyloxy, alkylthio, cycloalkyl, cycloalkyloxy, a nitro, hydroxy, phenoxy, trialkylsilyloxy group, —ONa, —OK, —OC(O)$R^7$, —OCHR$^8$C(O)$R^7$, —OC(O)NR$^8$R$^9$, —OS(O)$_2$R$^8$, —OS(O)$_2$NR$^8$R$^9$, —OP(X$^1$) (OR$^8$)OR$^9$, —OP(X$^1$) (R$^8$)R$^9$, —S(O)R$^8$, —S(O)$_2$R$^8$, or $R^4$ and $R^5$ may be taken together to represent an optionally substituted alkylene or alkyleneoxy chain; n is 0, or an integer of 1 or 2; $R^6$ independently represents a halogen atom, an optionally substituted alkyl, alkenyl, alkynyl, alkoxy, alkenyloxy, alkynyloxy, cycloalkyl, cycloalkoxy, hydroxy, —OC(O)$R^{10}$ group, or when R5 and R6 are attached to adjacent carbon atoms, $R^5$ and one $R^6$ may be taken together to represent —CH=CH—CH=CH— or an optionally substituted oxyalkyleneoxy chain; $R^7$ represents a hydrogen atom or an optionally substituted alkyl, alkoxy or aryl group; $R^8$, $R^9$ and $R^{10}$ independently represent a hydrogen atom, an alkyl, aryl or aralkyl group, or $R^8$ and $R^9$ may be taken together to represent an alkylene chain optionally interrupted by an oxygen or nitrogen atom; X represents an oxygen atom, a sulphur atom or a group NOR; $X^1$ represents an oxygen or sulphur atom; Y represents an oxygen or sulphur atom or a sulphonyl or sulphinyl group; and R represents a hydrogen atom or an optionally substituted alkyl, aralkyl, aryl or acyl group.

As used in the specification and claims, the term "benzophenone" encompasses oxime derivatives of benzophenone (X=NOR), benzothiophenones (X=S) and the underivatized benzophenone ketone (X=O).

The present invention also provides crop protection methods, fungicidal benzophenone compounds of formula Ia, methods of preparation of said benzophenone compounds and fungicidal compositions comprising at least one formula I or Ia compound and an agriculturally acceptable carrier.

DETAILED DESCRIPTION OF THE INVENTION

Huge economic losses have resulted from the devastation and damage of important agronomic and horticultural crops caused by fungal infection and infestation. Pest management strategies, field resistance, and virulent strains have all contributed to agriculturalists'concerns for combatting phytopathogenic fungal disease. In particular, ascomycetes, the causative agents for powdery mildew diseases continues to be a serious concern in cereal crop and fruit production. Further, in a variety of fungicidal agent applications concomitant phytotoxic injury to the host plant may be observed.

It has now been found that benzophenone compounds of formula I are highly effective fungicidal agents and are particularly effective for controlling mildew diseases such as powdery mildew. Compounds of formula I useful in fungus control methods are those benzophenones having the structure

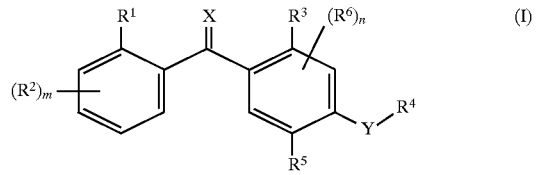

wherein X, Y, $R^1$, $R^2$, $R^3$, $R^4$, $R^5$, $R^6$, m and n are described hereinabove.

Alkyl as a substituent or as a part of other substituents, such as alkoxy or alkylthio may be straight-chain or branched and may contain up to eighteen, preferably up to 14, and especially up to 10, carbon atoms, individual examples including: methyl, ethyl, propyl, butyl, pentyl, hexyl, etc. as well as their isomers such as isopropyl, isobutyl, tertiary-butyl, isopentyl, and the like. Lower alkyl or alkoxy groups have from 1 to 10 carbon atoms. A cycloalkyl moiety as a substituent or as a part of other substituents suitably contains from 3 to 10, preferably from 3 to 6, carbon atoms. An alkenyl or alkynyl group suitably has from 2 to 6, preferably from 2 to 4 chain members, for example, ethenyl, propenyl, allyl, butenyl and the like as well as for chains with more than one double bond such as pentadienyl and the like. An alkylene chain usefully has 1 to 5, preferably 1 to 4, members.

An acyl group is formally formed by the removal of hydroxyl from a carboxyl group, and is used herein to include formyl and optionally substituted alkylcarbonyl and arylcarbonyl groups.

A halogen atom represents fluorine, chlorine, bromine and iodine, preferably chlorine. Preferred haloalkyl moieties are difluoromethyl and trifluoromethyl.

Optionally substituted moieties may be unsubstituted or have from one up to the maximal chemically possible number of substituents. Optional substituents may be any of those customarily employed in the development of biocidal compounds, and/or the modification of such compounds to influence their activity, persistence, penetration and any other property. Specific examples of such substituents include halogen, especially fluorine, chlorine or bromine, nitro, cyano, hydroxy, carboxy, amino, alkyl- or aralkylamino, dialkylamino, cycloalkylamino, piperidyl, piperidinyl, morpholinyl, carbamoyl, aryl- or benzylcarbamoyl, mono- or dialkylcarbamoyl, morpholinocarbonyl, trialkylsilyl, alkyl, alkenyl, alkynyl, alkoxy, alkoxyalkyl, alkoxyalkoxy, cycloalkyl, cycloalkoxy, acyl, optionally substituted benzoyl, benzoxazolyl, alkoxycarbonyl, optionally substituted pyridyl, phenoxy or naphthyl, phenyl or phenyl substituted by one or more substituents selected from the group comprising halogen, alkyl, alkoxy, alkoxyalkyl, alkoxyalkoxy, alkylthio, phenylthio, benzylthio, aralkoxy, hydroxy, carboxy, carbalkoxy, cyano, optionally substituted amino, nitro, trifluoromethyl, trifluoromethoxy and the like. Alkyl moieties of such optional substituents may have from 1 to 6 carbon atoms, preferably 1 or 2 carbon atoms. If a substituted group mentioned herein does contain two or more substituents, such substituents may be identical or different.

The benzophenone compounds according to formula I are oils, gums, or, predominantly, crystalline solid materials and possess valuable fungicidal properties. For example, they can be used in agriculture, or related fields such as horticulture and viticulture, for the control of phytopathogenic fungi, especially ascomycetes, and powdery mildew disease such as *Erysiphe graminis, Podosphaera leucotricha, Uncinula necator* and the like. Said benzophenone compounds possess a high fungicidal activity within a wide concentration range and may be used in agriculture without harmful phytotoxic effects.

Preferred formula I compounds useful in the method of invention are those in which $R^1$ represents a halogen atom or an optionally substituted alkyl or alkoxy group; m is 0 or an integer of 1, 2 or 3; and $R^2$ independently represents a halogen atom or an optionally substituted alkyl or alkoxy group; or $R^1$ and $R^2$ together represent —CH=CH—CH=CH—, oxyalkyleneoxy, difluorooxymethyleneoxy or alkylene; $R^3$ represents a halogen atom, an optionally substituted alkyl, alkenyl, alkylthio or alkylsulphonyl group, a nitro group, or an optionally substituted amino group; $R^5$ represents a hydrogen atom, an optionally substituted alkyl, alkoxy, alkenyloxy, alkynyloxy, cycloalkoxy or alkylthio group, a hydroxy group, a trialkylsilyloxy group, or a —OC(O)$R^7$, —OCHR$^8$C(O)$R^7$, —OC(O)NR$^8$R$^9$, NH—CO—$R^7$, —OS(O)$_2$R$^8$ or —OS(O)$_2$NR$^8$R$^9$ group; or $R^4$ and $R^5$ together represent an optionally substituted alkyleneoxy chain; n is 0 or the integer 1; $R^6$ represents an optionally substituted alkyl, alkenyl, alkynyl, alkoxy, alkenyloxy, alkynyloxy, cycloalkyl or cycloalkoxy group or a —OC(O)$R^{10}$ group; $R^7$ represents a hydrogen atom or an alkyl or alkoxy group; X represents an oxygen atom or an NOR group; and R represents a hydrogen atom or an optionally substituted alkyl group.

Good control of phytopathogenic fungi is obtained with a fungicidally effective amount of a compound of formula I wherein $R^1$ represents a halogen atom or an optionally substituted lower alkyl group; m is an integer of 1 or 3; $R^2$ independently represents a halogen atom or an optionally substituted lower alkyl group; $R^3$ represents a halogen atom, an optionally substituted alkyl or alkenyl group, or an optionally substituted amino group; $R^5$ represents an optionally substituted alkyl, alkoxy, alkenyloxy, alkynyloxy, cycloalkoxy or alkylthio group or $R^4$ and $R^5$ may be taken together to represent an optionally substituted alkyleneoxy chain; n is 0 or the integer 1; $R^6$ represents an optionally substituted alkyl, alkenyl, alkynyl, alkoxy, alkenyloxy, alkynyloxy, cycloalkyl or cycloalkoxy group or a —OC(O)$R^{10}$ group; $R^7$ represents an alkyl or alkoxy group; X represents an oxygen atom or NOR group; Y represents an oxygen atom; and R represents hydrogen or $C_1$–$C_4$alkyl.

Especially preferred are those formula I compounds in which $R^1$ represents a halogen atom or $C_1$-$C_4$alkyl group; $R^2$ independently represents a halogen atom or $C_1$–$C_4$alkyl group; $R^3$ represents a halogen atom or an optionally substituted $C_1$–$C_4$alkyl group; $R^4$ represents an optionally substituted $C_1$–$C_4$alkyl group; $R^5$ represents an optionally substituted lower alkyl, alkoxy, alkenyloxy, alkynyloxy or cycloalkoxy group; $R^6$ represents an optionally substituted $C_1$–$C_6$ alkoxy, alkenyloxy, alkynyloxy or cyloalkoxy group Effective control of phytopathogenic fungi may be achieved, for example, with a fungicidally effective amount of one or more of the following compounds:

2,3,5,6-tetramethyl-4',5',6'-trimethoxy-2'-methylbenzophenone;

2,6-dichloro-4',5'-dimethoxy-2'-methylbenzophenone-O-methyloxime;

2,6-dichloro-5'-t-butoxy-4'-methoxy-2'-methylbenzophenone;

2,6-dichloro-5',6'-di-n-butoxy-4'-methoxy-2'-methylbenzophenone;

2'-allyloxy-2,6-dichloro-3',4'-dimethoxy-6'-methylbenzophenone;

2'-benzyloxy-2,6-dichloro-3',4'-dimethoxy-6'-methylbenzophenone;

2'-butoxy-2,6-dichloro-3',4'-dimethoxy-6'-methylbenzophenone;

2'-cyclohexylmethoxy-2,6-dichloro-3',4'-dimethoxy-6'-methylbenzophenone;

2'-benzoylmethoxy-2,6-dichloro-3',4'-dimethoxy-6'-methylbenzophenone;

2'-cyclopentyloxy-2,6-dichloro-3',4'-dimethoxy-6'-methylbenzophenone;

2,6-dichloro-2',3',4'-trimethoxy-6'-methylbenzophenone;

2,6-dichloro-2'-ethoxy-3',4'-dimethoxy-6'-methylbenzophenone;

2,6-dichloro-2'-heptyloxy-3',4'-dimethoxy-6'-methylbenzophenone;

2,6-dichloro-2'-hexyloxy-3',4'-dimethoxy-6'-methylbenzophenone;

2,6-dichloro-3',4'-dimethoxy-2'-(2-methoxy-ethoxy)-6'-methylbenzophenone;

2,6-dichloro-3',4'-dimethoxy-6'-methyl-2'-(3-methylbutoxy) benzophenone;
2,6-dichloro-3',4'-dimethoxy-6'-methyl-2'-(prop-2-ynyloxy) benzophenone;
2,6-dichloro-3',4'-dimethoxy-6'-methyl-2'-pentyloxybenzophenone;
2,6-dichloro-3',4'-dimethoxy-6'-methyl-2'-propoxybenzophenone;
2,6-dichloro-4',5'-dimethoxy-2'-methylbenzophenone;
2,6-dichloro-4'-methoxy-2'-methyl-5'-(3-methylbutoxy) benzophenone;
2,6-dichloro-4'-methoxy-2'-methyl-5'-(prop-2-ynyloxy) benzophenone;
2,6-dichloro-4'-methoxy-2'-methyl-5'-(octyloxy) benzophenone;
2,6-dichloro-4'-methoxy-2'-methyl-5'-(pentyloxy) benzophenone;
2,6-dichloro-4'-methoxy-2'-methyl-5'-propoxybenzophenone;
2,6-dichloro-4'-methoxy-2'-methyl-5'-trimethylsilanylmethoxybenzophenone;
2,6-dichloro-5'-(1-ethyl-propoxy)-4'-methoxy-2'-methylbenzophenone;
2,6-dichloro-5-difluoromethoxy-4'-methoxy-2'-methylbenzophenone;
2,6-dichloro-5'-ethoxy-4'-methoxy-2'-methylbenzophenone;
2,6-dichloro-5'-heptyloxy-4'-methoxy-2'-methylbenzophenone;
2,6-dichloro-5'-hexyloxy-4'-methoxy-2'-methylbenzophenone;
2,6-dichloro-5'-isobutoxy-4'-methoxy-2'-methylbenzophenone;
2,6-dichloro-5'-isopropoxy-4'-methoxy-2'-methylbenzophenone;
5'-butoxy-2,6-dichloro-4'-methoxy-2'-methylbenzophenone;
5'-cyclohexylmethoxy-2,6-dichloro-4'-methoxy-2'-methylbenzophenone;
5'-cyclohexyloxy-2,6-dichloro-4'-methoxy-2'-methylbenzophenone;
5'-cyclopentyloxy-2,6-dichloro-4'-methoxy-2'-methylbenzophenone;
5'-cyclopropylmethoxy-2,6-dichloro-4'-methoxy-2'-methylbenzophenone; or
5'-decyloxy-2,6-dichloro-4'-methoxy-2'-methylbenzophenone.

Compounds of particular fungicidal use are those compounds of Formula I B.

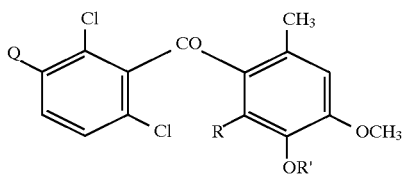

wherein Q represents a hydrogen or a chlorine atom; R represents a hydrogen atom, a $C_3$–$C_8$ cycloalkoxy group or a $C_1$–$C_8$-alkoxy group optionally substituted with one or more fluorine atoms, or one phenyl, phenoxy, phenylthio or benzyloxy group, wherein the phenyl moiety may be substituted by halogen, $C_1$–$C_4$-alkyl, $C_1$–$C_4$-alkoxy, trifluoromethyl or trifluoromethoxy; and R' represents hydrogen or $C_1$–$C_{10}$-alkyl optionally substituted with one or more halogen, $C_1$–$C_4$-alkoxy, phenyl, phenoxy or phenylthio groups, wherein the phenyl moiety may be substituted by halogen, $C_1$–$C_4$-alkyl, $C_1$–$C_4$-alkoxy, trifluoromethyl or trifluoromethoxy, with the proviso, that when Q and R represent hydrogen then R' must be other than methyl.

Preferred compounds of formula I B are those wherein Q represents a hydrogen or a chlorine atom; R represents a hydrogen atom, a $C_5$–$C_7$-cycloalkoxy group, a $C_1$–$C_6$-alkoxy group optionally substituted by one or more fluorine atoms, or one phenyl, phenoxy, phenylthio or benzyloxy group, wherein the phenyl moiety may be substituted by halogen, methyl, methoxy, trifluoromethyl or trifluoromethoxy; and R' represents hydrogen or $C_1$–$C_8$-alkyl optionally substituted by fluorine, chlorine, $C_1$–$C_4$-alkoxy, phenyl, phenoxy or phenylthio, wherein the phenyl moiety may be substituted by fluorine, chlorine, bromine, methyl, methoxy, trifluoromethyl or trifluoromethoxy.

Further compounds of particular value are those compounds of Formula I C.

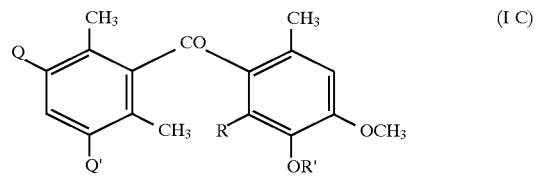

wherein Q and Q' independently represent a hydrogen atom or methyl group; R represents a hydrogen atom, a $C_3$–$C_8$-cycloalkoxy group or a $C_1$–$C_8$-alkoxy group optionally substituted with one or more fluorine atoms, a phenyl, phenoxy, phenylthio or benzyloxy group, wherein the phenyl moiety may be substituted with one or more halogen, $C_1$–$C_4$-alkyl, $C_1$–$C_4$-alkoxy, trifluoromethyl or trifluoromethoxy groups; and R' represents hydrogen or $C_1$–$C_{10}$-alkyl optionally substituted with one or more halogen, $C_1$–$C_4$-alkoxy, phenyl, phenoxy or phenylthio groups, wherein the phenyl moiety may be substituted by one or more halogen, $C_1$–$C_4$-alkyl, $C_1$–$C_4$-alkoxy, trifluoromethyl or trifluoromethoxy groups.

Preferred compounds of formula I C are those compounds, wherein Q and Q' independently represent a hydrogen atom or a methyl group; R represents a hydrogen atom, a $C_5$–$C_7$-cycloalkoxy group, a $C_1$–$C_6$-alkoxy group optionally substituted with one or more fluorine atoms, one phenyl, phenoxy, phenylthio or benzyloxy group, wherein the phenyl moiety may be substituted by fluorine, chlorine, bromine, methyl, methoxy, trifluoromethyl or trifluoromethoxy; and R' represents hydrogen or $C_1$–$C_8$-alkyl optionally substituted by one or more fluorine, chlorine, $C_1$–$C_4$-alkoxy, phenyl, phenoxy or phenylthio groups, wherein the phenyl moiety may be substituted with one or more bromine, methyl, methoxy, trifluoromethyl or trifluoromethoxy groups.

The present invention also provides new benzophenone compounds of formula Ia

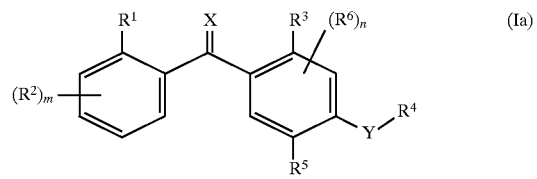

wherein $R^1$ represents a halogen atom, an optionally substituted alkyl group or a cyano group; m is an integer of 2, 3 or 4; $R^2$ independently represents a halogen atom, an optionally substituted alkyl or alkoxy group or when $R^1$ and $R^2$ are on adjacent carbon atoms, $R^1R^2$ together represent —CH=CH—CH=CH— or an optionally substituted alkylene or oxyalkyleneoxy group; $R^3$ represents a hydrogen or halogen atom, an optionally substituted alkyl, alkoxy, alkenyl, alkylthio, alkylsulphinyl, alkylsulphonyl, cyano, carboxy, hydroxy, nitro, or an optionally substituted amino group; $R^4$ represents an optionally substituted alkyl or acyl group; $R^5$ represents a halogen atom, an optionally substituted alkoxy, alkenyloxy, alkynyloxy, alkylthio, cycloalkyl, cycloalkyloxy, trialkylsilyloxy, —ONa, —OK, —OC(O)$R^7$, —OCHR$^8$C(O)$R^7$, —OC(O)NR$^8$R$^9$, —OS(O)$_2$R$^8$, —OS(O)$_2$NR$^8$R$^9$, -OP(X) (OR$^8$)OR$^9$, —OP($X^1$) (R$^8$)R$^9$, —S(O)R$^8$ or —S(O)$_2$R$^8$ group or $R^4$ and $R^5$ may be taken together to represent an optionally substituted alkylene or alkyleneoxy chain; n is 0 or an integer of 1 or 2; $R^6$ independently represents an optionally substituted alkoxy group, a hydroxy group or a —OC(O)$R^{10}$ group when attached to adjacent carbon atoms, or $R^5$ and one $R^6$ may be taken together to represent —CH=CH—CH=CH— or an optionally substituted oxyalkyleneoxy chain; $R^7$ represents a hydrogen atom or an optionally substituted alkyl, aryl or alkoxy group; $R^8$, $R^9$ and $R^{10}$ independently represent a hydrogen atom or an alkyl group, or $R^8$ and $R^9$ may be taken together to represent an alkylene chain optionally interrupted by an oxygen or nitrogen atom; X represents an oxygen atom, a sulphur atom or an NOR group; $X^1$ represents an oxygen or sulphur atom; Y represents an oxygen or sulphur atom or a sulphonyl or sulphinyl group; and R represents a hydrogen atom or an optionally substituted, alkyl, aralkyl, aryl or acyl group, with the provisos that when X represents an oxygen or sulphur atom and:

(i) when $R^1$ represents a halogen atom, then $(R^2)_m$ must be other than a halogen atom or no more than one alkyl or alkoxy group.
(ii) when $R^1$ represents an alkyl group, then $R^2$ must be other than alkyl;
(iii) when m is 1, then $R^2$ must be other than an alkoxy group;
(iv) when $R^3$ represents an alkenyl group, then $R^3$ cannot be substituted with an alkoxy or acyl group;
(v) when $R^3$ represents a haloalkyl group, then $R^1$ and $R^2$ must be other than a haloalkyl group; and
(vi) when Y represents an oxygen atom, then $R^3$ and $R^5$ must be other than a hydrogen atom and n must be 1 or 2.

The compounds of formula I can be prepared by conventional methods.

Thus the compounds having formula I (including those of formula Ia) may be prepared by a process which comprises reacting a compound of formula II

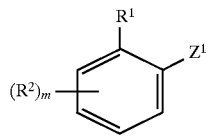
(II)

with a compound of formula III

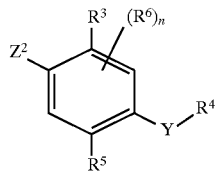
(III)

wherein $R^1$, $R^2$, $R^3$, $R^4$, $R^5$, $R^6$, Y, m and n are as hereinbefore defined and one of $Z^1$ and $Z^2$ represents a hydrogen atom and the other represents the group COCl; or one represents a magnesium halide group MgHal, wherein Hal is a halogen, preferably bromine or iodine, atom, and the other represents COCl or an aldehyde or nitrile group, followed in the last two cases by oxidation or hydrolysis, respectively, and optionally followed by further derivatization.

The starting materials of formula II and III are known products, and may themselves be prepared according to established methods or routine adaptations thereof. Substituents $R^1$ to $R^9$ which are not compatible with the selected reaction conditions may be introduced after formation of the benzophenone. They may be generated by known methods such as subsequent derivatization or substitution of a suitable group or by cleaving off a suitable protecting group.

When one of $Z^1$ and $Z^2$ is hydrogen and the other is COCl, the process is a Friedel Crafts reaction and is effected in the presence of a Lewis acid catalyst according to well-established procedures. Suitable catalysts include FeCl$_3$, AlCl$_3$, SnCl$_4$, ZnCl$_2$, TiCl$_4$, SbCl$_5$ and BF$_3$, which may be in a molar equivalent amount (based on the acyl chloride). However, it is also possible to use lesser amounts of catalyst at elevated temperatures, suitably under reflux temperatures, preferred catalysts under these conditions being FeCl$_3$, I$_2$, ZnCl$_2$, iron, copper, strong sulphonic acids such as F$_3$CSO$_3$H, and acidic ion exchange resins such as Amberlyst® 15 and Nafion®. The preferred catalyst is FeCl$_3$ in a 0.001 to 0.2 molar ratio at a temperature of about 50° to 180° C. The reaction can be carried out in a solvent inert under the reaction conditions, for example ethylene or methylene chloride, benzene, octane, decane or solvent mixtures, or in the absence of solvent, conveniently by employing one of the reactants in excess, e. g. in the range of 1:5 to 5:1. If AlCl$_3$ is being used, the molar ratio is preferably in the range of 0.5 to 2 and the suitable solvents are e.g. methylenechloride or ethylenechloride at a temperature usually between −10° and −70° C. If in the starting material R3 is methyl and R$_6$ or one R$_6$ represents a 5-alkoxy group (formula III) ether cleavage is possible to give the 6-hydroxy compound which then can be derivatized according to usual methods.

If the compound of formula II represents 2,6-dichlorobenzoylchloride and the compound of formula III is 1,2,3-trialkoxy-5-alkylbenzene, the Friedel-Crafts reaction with AlCl$_3$ can be used to prepare different products dependent on the reaction conditions. In case of a molar amount of 0.5 to 2 of aluminiumchloride, a temperature of about 0° to 25° C. and a solvent such as methylene or ethylene, the ether cleavage takes place in the 6-position (ortho position) of the compound of formula I within about 1 to 20 hours; at a higher temperature (about 40° C.) with—if necessary—longer reaction times (between about 2 and 24 hours) ether cleavage can be performed in the 5-(meta)-position too.

The processes described below can analogously be applied to other starting compounds, if desired.

Starting from compounds of formula

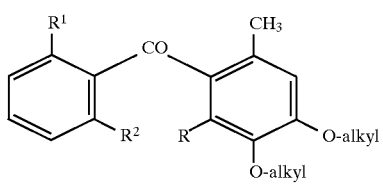
(VIII)

wherein $R^1$, $R^2$ represent preferably Cl, CH$_3$, R is H or O-alkyl and alkyl is preferably methyl, ether cleavage between about 50° and 100° C. with HBr/acetic acid leads to compounds of formula

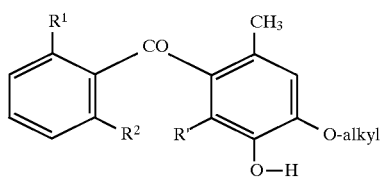

wherein R' is H or OH.

Starting from a compound of formula

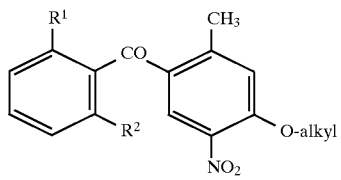

wherein $R^1$ and $R^2$ are defined as before, the cleavage of the O-alkyl group can be carried out with $AlCl_3$ (0.5–2 mol) in an inert solvent such as methylenechloride at about 20°–50° C. to give the corresponding OH compound.

The alkylation of compounds of formula VIII, IX or the ether cleavage product received from X can be carried out according to usual methods.

Compounds of formula IX wherein R' is H can be reacted with an alkylhalogenide (wherein the alkyl moiety may be substituted) in a lower alcohol in the presence of a basic compound such as potassium carbonate at elevated temperatures (e.g. 60°–150° C.).

In case of hydroxy groups in other positions (as in VIII, R'=OH or in the reaction product received from X) a salt with a metal has to be produced by reacting the hydroxy compound with e.g. potassium hydroxide. The salt is then reacted with an optionally substituted alkyl halogenide in a polar solvent (e.g. dimethylformamide) in the absence of water.

Dialkylation of compounds of formula IX wherein R' is OH with the same optionally substituted alkyl groups can be carried out starting from the corresponding di-alkali, preferably di-sodium salt, which can be obtained from the dihydroxy compound and sodium hydride in an inert solvent (e.g. tetrahydrofurane), the salt is then reacted in an inert polar solvent (e.g. dimethylformamide) with an excess of the optionally substituted alkylhalogenide at a temperature between about 80° and 120° C.

Dialkylation with a dihalogen compound of formula Hal-$(CH_2)_n$-Hal (Hal=Cl, Br or I; n=1 to 4) leads to cyclisation (compound XI; n as before):

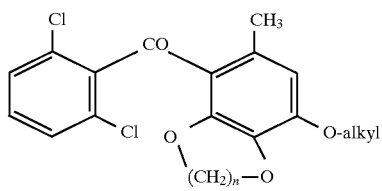

The reaction of the dihydroxy compound IX (R'=OH) with the dihalogen compound is carried out in the presence of an excess of potassium carbonate and of a small amount of copperoxide as catalyst at temperatures between about 10° and 50° C., preferably at room temperature.

To prepare acylated compounds a corresponding hydroxy compound, for example of formula XII

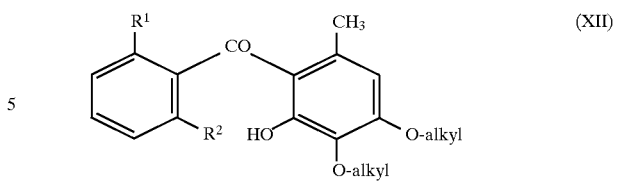

wherein $R_1$ and $R_2$ are Cl or $CH_3$, is reacted in form of its (e.g. potassium) salt in an inert polar solvent, such as dimethylformamide, with an optionally substituted acid chloride at a temperature between about 10° to 50° C.

Acylation of compounds of formula IX (with R'=H) can be carried out by heating that compound with an acid anhydride in the presence or without an inert solvent at temperatures between about 80° and 120° C.

For the preparation of compounds of formula XIII,

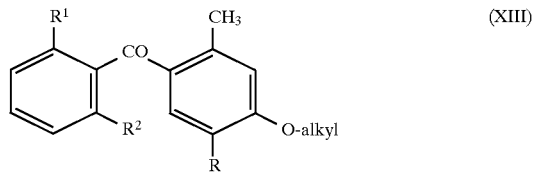

wherein R represents a t-butoxy group, $R^1$ and $R^2$ are defined as before but preferably represent Cl, the corresponding hydroxy compound (XIII; R=OH) is dissolved in an innert solvent, the solution cooled to about −70° C. and after addition of a catalytical amount of trifluoromethane sulfonic acid a stream of 2-methylpropene is bubbled into the mixture for 2 to 6 hours. After neutralizing the acid, the resulting t-butoxy compound can be isolated.

A 5-nitro compound of formula XIV

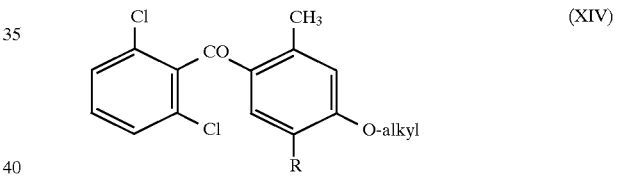

(R=$NO_2$) can be prepared by nitration of the corresponding compound unsubstituted in the 5-position (R=H) with concentrated (65%) nitric acid at about 50° to 100° C.

Nitration of compounds of formula XV

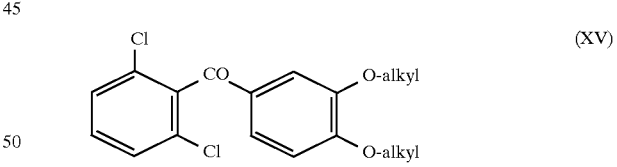

in the 2-position can be carried out with concentrated (65%) nitric acid at about 30° to 60° C.

The resulting or otherwise prepared nitro compounds can be reduced to the corresponding amino compounds, e. g. of formula XVI

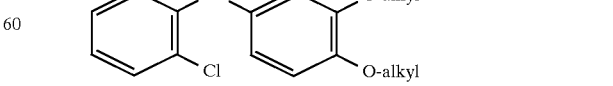

with excess powdered iron in a mixture of water/acetic acid 50:1 at elevated temperature (60° to 100° C.).

Reaction of the amino compounds with excess formic acid at reflux temperature leads to formylation of the amino group.

Compounds of formula XIV (R=H) can be brominated in 5-position when the equimolar amount of bromine (e. g. in trichloromethane) is added dropwise to the solution of the compound in trichloromethane at 10° to 30° C.

Benzophenothiones (I; X=S) can be prepared from the corresponding benzophenones by heating them with phosphorus pentasulfide in an inert solvent to reflux temperature for 2 to 10 hours.

When the magnesium halide is reacted with a nitrile, i.e. the other group $Z^1$ or $Z^2$ (formulae II, III) represents CN, the immediate reaction product is an imine of formula IV:

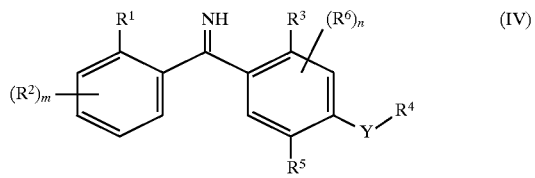

This intermediate is readily converted to the desired benzophenone derivatives of formula I wherein X is an oxygen atom by acid hydrolysis, suitably using mineral acids such as hydrochloric or sulphuric.

When magnesium halide is reacted with an aldehyde, i.e. the other group $Z^1$ or $Z^2$ represents CHO, the immediate reaction product is a tertiary alcohol of formula V:

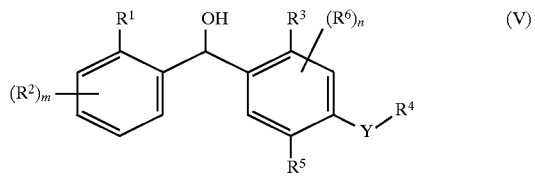

This formula V intermediate is readily converted to the desired benzophenone derivatives of formula I wherein X is an oxygen atom by oxidation, suitably using Mn(IV), Mn(VII), Ce(IV) or Cr(VI) derivatives, nitric acid or oxygen in the presence of a catalyst.

Certain oxime derivatives of formula I may be prepared by reacting the appropriately substituted nitrile oxide of formula VI with a suitable o-dimethoxybenzene of formula VII in the presence of aluminum chloride and an inert solvent to form an intermediate and hydrolyzing the intermediate in aqueous acid to give the desired product compounds of Ib. The reaction is shown in flow diagram I.

FLOW DIAGRAM I

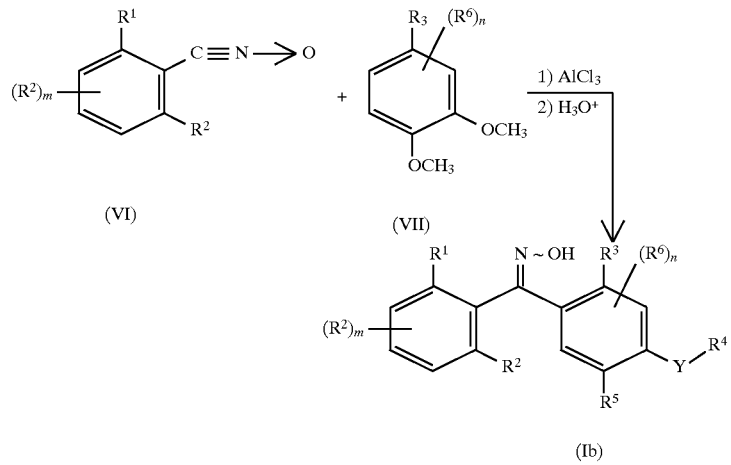

For compounds of formula Ib the substituents $R^1$, $R^2$, $R^3$, $R^6$ and n as defined hereinabove for formula I and Ia and m is 0 or an integer of 1, 2 or 3. The oximes of formula Ib may be O-alkylated or O-acylated using conventional alkylation and acylation techniques.

The substituents of the benzophenones produced according to the processes of the invention may be derivatized further according to established methods or routine adaptations thereof, such as hydrogenation, acylation, cleavage of ether bonds, alkylation or nitration.

The formula Ia compounds of the invention are excellent fungicides, especially for the control of phytopathogenic fungi in agriculture or related fields. They are useful for the control of powdery mildew diseases, particularly of *Erysiphe graminis, Podosphaera leucotricha* or *Uncinula necator*. Due to excellent plant tolerance, the compounds may be used in all cultivation of plants where infection by the controllable fungi is not desired, e.g. small grain cereals, apples, vine. The absence of target crop phytotoxicity at fungus control rates is a feature of the present invention.

The present invention also provides a fungicidal composition which comprises a compound of formula I or Ia as defined hereinabove and an agriculturally acceptable carrier. Said composition may contain one or more compounds of the present invention. Preferably, at least one carrier in a composition according to the invention is a surface-active agent. For example, the composition may contain at least two carriers, at least one of which is a surface-active agent.

The compounds according to formula I or Ia may be applied as technical material, however, said compounds are preferably applied as a composition comprising, besides the formula I or Ia compounds, adjuvants and auxiliaries which are known for formulation purposes and are manufactured into e.g. emulsion concentrates, solutions which may be sprayed directly or diluted, diluted emulsions, wettable powders, soluble powders, dusts, granulates, microencapsulates by well-established procedures. The form of application such as spraying, atomizing, dispersing, pouring may be chosen like the compositions according to the desired objectives and the given circumstances.

It is contemplated, compounds of formula I or Ia may be formulated or applied, either alone or in combination, with one or more pesticides or plant growth regulants. Pesticides used in combination may be herbicides, insecticides or other fungicides or a combination thereof. When the formula I or Ia compounds are applied in combination with another pesticide or pesticides, they may be applied simultaneously or sequentially. Among the available fungicides which may be used in combination with formula I compounds are 4,6-dinitro-o-cresol, benalaxyl, benomyl, captafol, captan, carbendazim, chlorothalonil, copper, cymoxanil, dichlofluanid, dichlone, difenoconazole, dimethomorph, diniconzole, dinocap, dithianon, fenpiclonil, fenpropiomorph, hymaxazol, imazalil, iprodione, isoprothiolane, kasugamycin, mancozeb, mepronil, mercuric oxide, oxadixyl, oxolinic acid, penconazole, propineb, pyrifenox, thiabendazole, thiram, tolclofos-methyl, triadimefon, triflumizole, triforine validamycin A, vinclozolin, zineb, ziram, and the like.

The fungicidal compositions of the invention may be prepared by well-established procedures, e.g. intensive mixing and/or grinding of the active ingredients with other substances, such as fillers, solvents, solid carriers, and optionally surface-active compounds (tensides).

Solvents may be aromatic hydrocarbons, preferably the fractions $C_8$ to $C_{12}$, e.g. xylenes or xylene mixtures, substituted naphthalenes, phthalic acid esters, such as dibutyl or dioctyl phthalate, aliphatic hydrocarbons, e.g. cyclohexane or paraffins, alcohols and glycols as well as their ethers and esters, e.g. ethanol, ethyleneglycol mono- and dimethyl ether, ketones such as cyclohexanone, strongly polar solvents such as N-methyl 2-pyrrolidone, dimethyl sulphoxide, alkyl formamides, epoxidized vegetable oils, e.g. epoxidized coconut or soybean oil, water.

Solid carriers, which may be used for dusts or dispersible powders, may be mineral fillers, such as calcite, talc, kaolin, montmorillonite, attapulgite. The physical properties may be improved by addition of highly dispersed silica gel or highly dispersed polymers.

Carriers for granulates may be porous material, e.g. pumice, broken brick, sepiolite, bentonite, non-sorptive carriers may be calcite or sand. Additionally, a multitude of pre-granulated inorganic or organic materials may be used, such as dolomite or crushed plant residues.

Suitable surface-active substances may be non-ionogenic, anionic or cationic tensides with good dispersing, emulgating and wetting properties depending on the nature of the benzophenone compound to be formulated. Tensides may also mean mixtures of tensides.

Suitable tensides may be so-called water-soluble soaps as well as water-soluble synthetic surface-active compounds. Soaps usually are alkali, earth alkali or optionally substituted ammonium salts of higher fatty acids ($C_{10}$–$C_{20}$), e.g. the sodium or potassium salts of oleic or stearic acid or of mixtures of natural fatty acids which are prepared, for example, from coconut or tallow oil. Furthermore, methyltaurine salts of fatty acids may be used. However, so-called synthetic tensides are preferably used, especially fatty sulphonates, fatty sulphates, sulphonated benzimidazole derivatives or alkyl aryl sulphonates. The fatty sulphates or fatty sulphonates are normally used as alkali, earth alkali or optionally substituted ammonium salts and have an alkyl moiety of 8 to 22 carbon atoms, whereby alkyl also means the alkyl moiety of acyl residues, such as the sodium or calcium salt of lignin sulphonic acid, of sulphuric acid dodecylate or of a mixture of fatty alcohols prepared from natural fatty acids. This also includes the salts of sulphuric acid esters, sulphonic acids and adducts of fatty alcohols and ethylene oxide. The sulphonated benzimidazole derivatives preferably contain 2 sulphonic acid residues and a fatty acid residue with 8 to 22 carbon atoms. Alkyl aryl sulphonates are, for example, the sodium, calcium or triethyl ammonium salts of dodecyl benzene sulphonic acid, dibutyl naphthalene sulphonic acid or of a condensate of naphthalene sulphonic acid and formaldehyde. Furthermore, phosphates, such as the salts of the phosphoric acid ester of a p-nonylphenol-(4-14)-ethylene oxide adduct or phospholipids, may be used.

Non-ionic tensides are preferably polyglycolether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols. Other suitable non-ionic tensides are the water-soluble, 20 to 250 ethylene glycol ether groups containing polyadducts of ethylene oxide and polypropylene glycol, ethylene diamino polypropylene glycol and alkyl polypropylene glycol with 1 to 10 carbon atoms in the alkyl moiety, the substances normally contain 1 to 5 ethylene glycol units per propylene glycol unit. Examples of non-ionic tensides are nonylphenol polyethoxy ethanols, castor oil polyglycol ether, polyadducts of ethylene oxide and polypropylene, tributyl phenoxy polyethoxy ethanol, polyethylene glycol, octyl phenoxy polyethoxy ethanol. Furthermore, fatty acid esters of polyoxy ethylene sorbitan, such as polyoxy ethylene sorbitan trioleate may be used.

Cationic tensides preferably are quaternary ammonium salts, which have at least one alkyl residue with 8 to 22 carbon atoms and, furthermore, low, optionally-halogenated alkyl, benzyl or hydroxyalkyl residues. The salts are preferably halides, methyl sulphates or alkyl sulphates, e.g. stearyl trimethyl ammonium chloride or benzyl bis(2-chloroethyl) ethyl ammonium bromide.

The tensides generally used for compositions of the invention are disclosed in publications such as: "McCutheon's Detergents and Emulsifiers Annual", MC Publishing Corp., Ridgewood, N.J., USA 1981; H. Stache, "Tensid-Taschenbuch", 2nd ed., C. Hanser, Munich, Vienna, 1981; M. and J. Ash, "Encyclopedia of Surfactants", vol. I–III, Chemical Publishing Co., New York, N.Y., USA 1980–1981.

The pesticidal compositions of the invention may comprise 0.1% to 95%, preferably 0.1% to 80% of at least one compound of formula I or Ia, 1% to 99.9% of a solid or liquid adjuvant and 0% to 25%, preferably 0.1% to 25%, of a tenside.

Exemplary of the compositions of the invention are:
Emulsion Concentrates
Active ingredient: 1% to 20%, preferably 5% to 10%
Surface-active substance: 5% to 30%, preferably 10% to 20% Liquid carrier: 50% to 94%, preferably 70% to 85%
Suspension-Concentrates
Active ingredient: 5% to 75%, preferably 10% to 50%
Water: 94% to 24%, preferably 88% to 30% Surface-active substance: 1% to 40%, preferably 2% to 30%
Wettable Powder
Active ingredient: 0.5% to 90%, preferably 1% to 80%
Surface-active substance: 0.5% to 20%, preferably 1% to 15% Solid carrier: 5% to 95%, preferably 15% to 90%
Dusts
Active ingredient: 0.1% to 10%, preferably 0.1% to 1%
Solid carrier: 99.9% to 90%, preferably 99.9% to 99%
Granulates
Active ingredient: 0.5% to 30%, preferably 3% to 15% Solid carrier: 99.5% to 70%, preferably 97% to 85%

As commodity the inventive fungicidal compositions may preferably be in a concentrated form whereas the end-user generally employs diluted compositions. Said compositions may be diluted to a concentration of 0.001% of active ingredient (a.i.). The doses usually are in the range from 0.01 to 10 kg a.i./ha.

Said compositions may also comprise other auxiliaries such as stabilizers, defoamer, viscosity controlling agents, thickeners, adhesives, fertilisers or other active ingredients to obtain special effects.

For a more clear understanding of the invention, the following specific examples are set forth below. These examples are merely illustrations and are not to be understood as limiting the scope and underlying principles of the invention in any way. Indeed, various modifications of the invention in addition to those shown and described herein will become apparent to those skilled in the art from the following examples and foregoing description. Such modifications are also intended to fall within the scope of the appended claims. The terms HNMR, CIMS and IR as used in the examples hereinbelow designate proton nuclear magnetic resonance, mass spectrum and infrared, respectively.

EXAMPLE 1

2,6-Dichloro-4',5'-dimethoxy-2'-methylbenzophenone (Compound 1)

($R^1$=Cl, $R^2$=6-Cl, R=$CH_3$, $R^4$=$CH_3$, $R^5$=$OCH_3$, X=O, Y=O, m=1, n=0)

A mixture of 4-methyl-veratrol (76.1 g; 500 mmol), 2,6-dichlorobenzoyl chloride (120.4 g; 575 mmol) and iron (III)chloride (0.5 g) is heated with stirring. The reaction starts at 90° C. under formation of hydrogen chloride, the main reaction is complete within 10 min at 95° C. Subsequently, the reaction mixture is stirred for another 30 min at 100° C. and then cooled to 65° C. Upon addition of methanol (350 ml) Compound 1 begins to crystallize. A water/methanol mixture (1:1 v/v; 300 ml) is then slowly added at 40° C. and the mixture is cooled to room temperature with stirring for 30 min. The solid material is collected by vacuum filtration, three times washed with methanol/water (3:1 v/v; 100 ml each) and dried yielding colorless crystals, 148.6 g, (91.4% y) mp 101.5° C.

EXAMPLE 2

Derivatization of benzophenones

A) 2.6-Dichloro-4',5'-dimethoxy-2'-nitro-benzophenone (Compound 2)

($R^1$=Cl, $R^2$=6-Cl, $R^3$=$NO_2$, $R^4$=$CH_3$, $R^5$=$OCH_3$, X=O, Y=O, m=1, n=0)

A portion of 2,6-dichloro-3',4'-dimethoxybenzophenone (6.22 g, 20 mmol), prepared analogously to Example 1, is added within 15 min into nitric acid (65%; 40 ml) which is heated to 40° C. The clear solution is stirred for 10 min at 40° C., then 1 h at room temperature. The reaction mixture is then poured into water whereupon a slowly solidifying oil forms. This material is dissolved in a small amount of N,N-dimethyl formamide under warming, then methanol is added and the mixture is chilled and filtered giving Compound 2 as yellow crystals, 5.57 g, (78% y) with mp 143° C.

B) 2'-Amino-2,6-dichloro-4',5'-dimethoxybenzophenone (Compound 3)

($R^1$=Cl, $R^2$=6-Cl, $R^3$=NHCHO, $R^4$==$CH_3$, $R^5$=$OCH_3$, X=O, Y=O, m=1, n=0)

A portion of 2,6-dichloro-3',4'-dimethoxy-2'-nitrobenzophenone (Compound 2; 3.56 g, 10 mmol) is added to a mixture of water (50 ml), glacial acetic acid (1 ml) and powdered iron (3.30 g, 60 mmol) within 15 min at 70° C. The reaction mixture is stirred at 95° C. for another 3 h. After cooling, toluene (50 ml) is added and the solid material removed by vacuum filtration. The filter cake is washed with toluene. The filtrate and washings are combined and washed with water, dried and then applied onto a flash chromatography column (silica gel, 50 g). The column is consecutively eluted with toluene, and toluene containing 1%, 2%, 5% and 10% of acetone (250 ml each). The fraction eluted by 10% acetone is concentrated in vacuo to a final volume of 10 ml whereby Compound 3 crystallizes yielding yellow crystals, 1.61 g, (49% y) mp 181° C.

C) 2,6-Dichloro-4',5'-dimethoxy-2'-formylamino-benzophenone (Compound 4)

($R^1$=Cl, $R^2$=6-Cl, $R^3$=NHCHO, $R^4$=$CH_3$, $R^5$=$OCH_3$, X=O, Y=O, m=1, n=0) n=0)

A mixture of 2'-amino-2,6-dichloro-4',5'-dimethoxybenzophenone (Compound 3; 0.82 g, 2.5 mmol) and formic acid (30 ml) is heated at reflux temperature for 24 h, and evaporated in vacuo. The residue is dissolved in a small amount of toluene, Compound 4 crystallizes upon addition of cyclohexane giving colorless crystals, 0.64 g, (72% y) with mp 152° C.

D) 2,6-Dichloro-5'-hydroxy-4'-methoxy-2'-methylbenzophenone (Compound 5)

($R^1$=Cl, $R^2$=6-Cl, $R^3$=$CH_3$, $R^4CH_3$, $R^5$=OH, X=O, Y=O, m=1, n=0)

A mixture of 2,6-dichloro-4',5'-dimethoxy-2'-methylbenzophenone (Compound 1; 2.5 g, 7.7 mmol), hydrogen bromide/acetic acid (33%, 10 ml) and glacial acetic acid (10 ml) is stirred for 1.5 h at 75° C., poured into water (100 ml) and twice extracted with dichloromethane (50 ml each). The extracts are combined, dried, and concentrated in vacuo. The resulting oil is applied onto the top of a flash chromatography column (silica gel, 30 g). Elution is carried out with toluene and toluene/acetone, 9:1 (500 ml each). The fractions containing the material with an $R_f$=0.54 (silica gel; toluene/acetone, 9:1) are combined and the solvent is evaporated in vacuo until a final volume of 20 ml is reached. The solution is then extracted three times with aqueous sodium hydroxide (2N; 30 ml each). The aqueous layer is acidified with hydrochloric acid (6M) and the precipitate is collected by vacuum filtration and dried to give Compound 5 as colorless crystals, 1.1 g, (45.9% y) mp 152° C.

E) 2,6-Dichloro-4'-methoxy-2 '-methyl-5 h-propoxy-benzophenone (Compound 6)

($R^1$=Cl, $R^2$=6-Cl, $R^3$=$CH_3$, $R^4$=$CH_3$, $R^5$=O-n-$C_3H_7$, X=O, Y=O, m=1, n=0)

A mixture of 2,6-dichloro-5'-hydroxy-4'-methoxy-2'-methylbenzophenone (Compound 5; 1.0 g, 3.2 mmol), n-propyl bromide (0.5 g, 4 mmol), potassium carbonate (2.8 g, 20 mmol) and ethanol (10 ml) is stirred for 6 h at 80° C., filtered and the filtrate is evaporated in vacuo. The residue is applied onto a flash chromatography column (silica gel, 30 g). Elution with toluene (750 ml) yields Compound 6 as a brown oil, 800 mg, (70.7% y) which slowly crystallizes (mp 73°–75° C.)

F) 2,6-Dichloro-4',5'-dimethoxy-2'-methyl-benzophenthione (Compound 7)

($R^1$=Cl, $R^2$=6-Cl, $R^3$=$CH_3$, $R^4$=O-$CH_3$, $R^5$=O-$CH_3$, X=S, Y=O, m=1, n=0)

A mixture of 2,6-dichloro-4',5'-dimethoxy-2'-methylbenzophenone (Compound 1; 3.25 g, 10.0 mmol), phosphorus pentasulphide (2.22 g, 10.0 mmol) and toluene (50 ml) is stirred at 110° C. for 5 h, treated with p-dioxane, stirred at 100° C. for a further 24 h. The supernatant is decanted from black, tarry reaction products, silica gel (15 g) is added and the solvent is evaporated in vacuo. A flash chromatography column is packed with silica gel (100 g) and the charged silica gel is layered on top of it. The column is subsequently eluted with petrol ether/acetone (500 ml, 98:2, v/v) and petrol ether/acetone (750 ml, 95:5, v/v) yielding Compound 7 as a dark green oil 40 mg, (1.2% y), which slowly solidifies. When the oil is triturated with cyclohexane three times, it gives a solid, mp 142° C.

EXAMPLE 3

Using essentially the same procedures described hereinabove for Examples 1 and 2 and employing standard derivatization techniques where appropriate, the following compounds are prepared and shown in Table I.

TABLE I

| Comp No. | R¹ | R² | R³ | R⁴ | R⁵ | R⁶ | Y | Mp °C. |
|---|---|---|---|---|---|---|---|---|
| 8 | Cl | 6-Cl | H | CH₃ | CH₃ | OC₂H₅ | H | O | 87 |
| 9 | Cl | 6-Cl | H | CH₃ | C₂H₅ | OCH₃ | H | O | 106 |
| 10 | Cl | 6-Cl | H | CH₃ | CH₃ | Cl | H | O | 168 |
| 11 | Br | 6-Cl | 3-NO₂ | CH₃ | CH₃ | OCH₃ | H | O | oil |
| 12 | Cl | H | H | CH₃ | CH₃ | OCH₃ | H | O | 69–71 |
| 13 | Cl | 6-Cl | H | CH₃ | CH₃ | OC(O)C₂H₅ | H | O | 142–145 |
| 14 | I | H | H | CH₃ | CH₃ | H | H | O | 89 |
| 15 | Cl | H | H | CH₃ | CH₃ | OCH₃ | H | O | 66–68 |
| 16 | Cl | 6-CH₃ | H | F | CH₃ | OCH₃ | H | O | 56 |
| 17 | Cl | 6-CH₃ | 6-Cl | CH₃ | CH₃ | OCH₃ | H | O | 95 |
| 18 | (CH=CH)₂ | H | CH₃ | CH₃ | OCH₃ | H | O | oil |
| 19 | I | 3-I | 5-I | CH₃ | CH₃ | OCH₃ | H | O | oil |
| 20 | Br | 5-Br | H | CH₃ | CH₃ | OCH₃ | H | O | 126–128 |
| 21 | Cl | 4-NO₂ | H | CH₃ | CH₃ | SCH₃ | H | O | 105 |
| 22 | Cl | 6-Cl | H | CH₃ | CH₃ | OCH₃ | 2-OCH₃ | S | 92 |
| 23 | Cl | 6-Cl | H | CH₃ | CH₃ | CH₂O | H | O | 142 |
| 24 | Cl | 6-Cl | H | CH₃ | CH₃ | I | H | S | oil |
| 25 | Cl | 5-OCH₃ | H | CH₃ | CH₃ | OCH₃ | H | O | 94–96 |
| 26 | Br | 5-Br | H | CH₃ | CH₃ | OC(O)CH–(CH₃)₂ | H | O | 132–135 |
| 27 | Cl | 6-Cl | H | CH₃ | CH₃ | OCH₃ | H | O | oil |
| 28 | Cl | 5-Cl | 6-OCH₃ | CF3 | CH₃ | Cl | H | O | 126–128 |
| 29 | Cl | 6-Cl | H | CH₃ | CH₃ | OCHF₂ | H | O | 98–101 |
| 30 | Cl | 6-Cl | H | CH₃ | CH₃ | OCH₃ | H | O | 100–125 |
| 31 | CF₃ | 5-CF₃ | H | CH₃ | CH₃ | OC(O)C–(CH₃)₃ | 3-OCH₃ | O | 167 |
| 32 | Cl | 6-Cl | H | CH₃ | H | OH | H | O | 201–203 |
| 33 | Cl | 6-Cl | H | SCH₃ | CH₃ | OCH₃ | H | O | 185 |
| 34 | Cl | 6-Cl | H | S(O₂)CH₃ | CH₃ | OCH₃ | H | O | 163 |
| 35 | Cl | 6-Cl | H | CH₃ | CH₃ | CH₃ | 3-CH₃ | O | 78 |
| 36 | Cl | 6-Cl | H | S(O)CH₃ | CH₃ | OCH₃ | H | O | 178 |
| 37 | Cl | 3-Cl | 5-Cl | CH₃ | CH₃ | OCH₂CH=CH₂ | H | O | oil |
| 38 | Cl | 6-Cl | H | CH₃ | CH₃ | OCH₃ | H | O | 99–101 |
| 39 | CF₃ | 6-CF₃ | H | CH₃ | CHF₂ | (CH₂)₂O | H | O | oil |
| 40 | Cl | 6-Cl | H | CH=CH₂ | CH₃ | OCHF₂ | H | O | 65–68 |
| 41 | Cl | 6-Cl | H | CH₃ | CH₃ | OCH₃ | H | O | 105–107 |

TABLE I-continued

![Structure showing benzophenone with R1, R2 on left ring, R3, R6 on right ring, R5, and Y-R4 substituent]

| Comp No. | R¹ | R² | R² | R³ | R⁴ | R⁵ | R⁶ | Y | Mp °C. |
|---|---|---|---|---|---|---|---|---|---|
| 46 | I | 6-F | H | CH₃ | CH₃ | OCH₃ | H | O | oil |
| 47 | Cl | 3-Cl | H | CH₃ | CH₃ | OC₂H₅ | H | O | 97 |
| 48 | Cl | 6-Cl | H | CH₃ | C₂H₅ | OC₂H₅ | H | O | 77 |
| 49 | Cl | 6-Cl | H | CH=CH—CN | CH₃ | OCH₃ | H | O |  |
| 50 | Cl | 4-Cl | 5-Cl | CH₃ | CH₃ | OCH₃ | 3-Br | O | 86 |
| 51 | Cl | 6-Cl | H | CH₃ | CH₃ | OCH₃ | H | O | 160 |
| 52 | Cl | 6-Cl | H | CH₃ | CH₃ | C₄H₉-t | H | O | 124 |
| 53 | Cl | 6-Cl | H | CH₃ | CH₃ | OC₄H₉-n | H | O | 51 |
| 54 | Cl | 6-Cl | H | CH₃ | CH₃ | OC₄H₉-i | H | O | oil |
| 55 | Cl | 6-Cl | H | CH₃ | CH₃ | H | H | O | S |
| 56 | Cl | 6-Cl | H | CH₃ | CH₃ | OCH₂C₆H₅ | H | O | 119–121 |
| 57 | Cl | 6-Cl | H | CH₃ | CH₃ | OC₅H₁₁-n | H | O | 46–48 |
| 58 | Cl | 6-Cl | H | CH₃ | CH₃ | OC₃H₇-i | H | O | oil |
| 59 | Cl | 6-Cl | H | CH₃ | CH₃ | OCH₂C(O)—OC₂H₅ | 2-OH | O | 161 |
| 60 | Cl | 6-Cl | H | CH₃ | CH₃ | OCH₃ | H | O | 105–108 |
| 61 | Cl | 6-Cl | H | CH₃ | CH₃ | H | 2-OCH₃ | O | 135 |
| 62 | Cl | 6-Cl | H | CH₃ | CH₃ | OCH₃ | 2-OC₂H₅ | O | 72 |
| 63 | Cl | 6-Cl | H | CH₃ | CH₃ | Cl | H | S |  |
| 64 | Cl | 4-Cl | 6-Cl | CH₃ | CH₃ | OCH₃ | H | S | 108–109 |
| 65 | Cl | 6-Cl | H | CH₃ | CH₃ | Br | H | O | 75 77 |
| 66 | F | 6-F | H | CH₃ | CH₃ | OCH₃ | H | O | oil |
| 67 | Cl | H | H | CH₃ | CH₃ | OCH₃ | H | O | oil |
| 68 | Cl | 4-Cl | H | CH₃ | CH₃ | OCH₃ | H | O | 135–138 |
| 69 | Cl | 6-Cl | H | CH₃ | CH₃ | CH₃ | H | O | 100–102 |
| 70 | Cl | 5-Cl | H | CF₃ | CH₃ | Br | H | O | oil |
| 71 | Cl | 6-Cl | H | CH₃ | CH₃ | OCH₃ | H | O | oil |
| 72 | Cl | 3-Cl | H | C₂H₅ | CH₃ | OCH₃ | H | O | 120 |
| 73 | Cl | 6-Cl | H | CH₃ | CH₃ | OCH₃ | H | O | oil |
| 74 | Cl | 6-Cl | H | CN | CH₃ | OCH₃ | H | O | 127 |
| 75 | F | 6-CF₃ | H | CH₃ | CH₃ | OCH₂CN | H | O | 72–73 |
| 76 | Cl | 6-F | H | CH₃ | CH₃ | OCH₃ | H | O | 101 |
| 77 | Cl | 6-Cl | H | I | CH₃ | OCH₃ | H | O | 72 |
| 78 | Cl | 6-Cl | H | C₃H₇-n | CH₃ | OCH₃ | H | O |  |
| 79 | Cl | 6-Cl | H | CH₃ | CH₃ | OC(O)CH₃ | H | O | 156–159 |
| 80 | Cl | 6-Cl | H | Br | CH₃ | OCH₃ | H | O | 124 |
| 81 | Cl | 6-Cl | H | CH₃ | CH₃ | OCH≡CH | H | O | 87 |
| 82 | Cl | 6-Cl | H | H | CH₃ | H | 3-OCH₃ | O | 127 |
| 83 | Cl |  |  |  |  |  |  |  |  |

TABLE I-continued

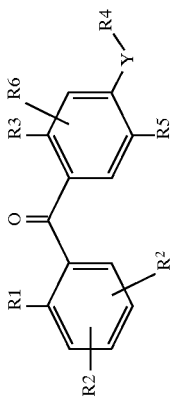

| Comp No. | R¹ | R² | R³ | R⁴ | R⁵ | R⁶ | Y | Mp °C. |
|---|---|---|---|---|---|---|---|---|
| 84 | Cl | 6-Cl | CH₃ | H | H | 3,6-di-CH₃ | O | 122 |
| 85 | Cl | 6-Cl | CH₃ | CH₃ | H | 3,6-di-CH₃ | O | 111 |
| 86 | CH₃ | 6-Cl | CF₃ | C(O)-2,6-C₁₂C₆H₃ | H | H | O | 186 |
| 87 | CH₃ | 6-CH₃ | H | CH₃ | H | 3-OCH₃ | O | 84 |
| 88 | Cl | 6-Cl | H | CH₃ | H | 3-Br | O | 129 |
| 89 | Cl | 6-Cl | H | CH₃ | Br | 3-OCH₃ | O | 140 |
| 90 | Cl | 6-Cl | OCH₃ | CH₃ | OC(O)H | H | O | 124 |
| 91 | OCH₃ | 6-OCH₃ | CH₃ | CH₃ | OCH₃ | H | O | 156 |
| 92 | Cl | 6-OCH₃ | CH₃ | CH₃ | OCH₃ | H | O | 113 |
| 93 | Cl | 6-Cl | COOH | CH₃ | OCH₃ | H | O | 174 |
| 94 | Cl | 6-Cl | CH₃ | CH₃ | S(O)₂CH₃ | H | SO₂ | 233 |
| 95 | Cl | 6-Cl | CH₃ | CH₃ | SOCH₃ | H | SO | 227 |
| 96 | Cl | 6-Cl | CH₃ | CH₃ | O$_n$-C₇H₁₅ | H | O | oil |
| 97 | Cl | 6-Cl | CH₃ | CH₃ | O$_n$-C₈H₁₇ | H | O | oil |
| 98 | CH₃ | 6-Cl | CH₃ | CH₃ | O$_n$-C₁₀H₂₁ | H | O | oil |
| 99 | CH₃ | 4-CH₃ | CH₃ | CH₃ | OCH₃ | H | O | 74 |
| 100 | Cl | 6-Cl | CH₃ | CH₃ | OCH₂-c-C₃H₅ | H | O | oil |
| 101 | Cl | 6-Cl | CH₃ | CH₃ | OCH₂-c-C₆H₁₁ | H | O | 108 |
| 102 | Cl | 6-Cl | CH₃ | CH₃ | O(CH₂)₂—CH(CH₃)₂ | H | O | oil |
| 103 | Cl | 6-Cl | CH₃ | CH₃ | OCH₂CH=C=C—(CH₃)₂ | H | O | oil |
| 104 | CH₃ | 6-Cl | CH₃ | CH₃ | OCH₃ | H | O | 90–92 |
| 105 | Cl | 6-Cl | CH₃ | CH₃ | Oc-C₅H₉ | H | O | oil |
| 106 | Cl | 6-Cl | CH₃ | CH₃ | Oc-C₆H₁₁ | H | O | oil |
| 107 | Cl | 6-Cl | H | CH₃ | [3]-[CH=CH—)₂-[2] | H | O | oil |
| 108 | Cl | 6-Cl | CH₃ | CH₃ | ONa | H | O | 155–157 |
| 109 | Br | 6-Br | CH₃ | CH₃ | OSi(CH₃)₃ | H | O | glass |
| 110 | Cl | 6-Cl | CH₃ | CH₃ | OCH₃ | H | O | 102 |
| 111 | Cl | 6-Cl | CH₃ | CH₃ | OK | 2-OCH₃ | O | 98 |
| 112 | CN | H | OCH₃ | CH₃ | Br | H | O | 183 |
| 113 | Cl | 6-Cl | CH₃ | CH₃ | OCH₃ | 2-OCH₃ | O | 76 |
| 114 | Cl | 6-Cl | NH—CH₃ | CH₃ | —CH₂O— |  |  | 98 |
| 115 | Cl | 6-Cl | OH | CH₃ | OCH₃ | H | O | 163 |
| 116 | Cl | H | CH₃ | CH₃ | OCH₂—Si(CH₃)₃ | H | O | 80 |
| 117 | Cl | 6-Cl | CH₃ | CH₃ | OCH₃ | H | O | oil |
| 118 | Cl | 3-Cl | CH₃ | CH₃ | OCH₃ | 2-OCH₃ | O | 62–64 |
| 119 | Cl | 4-Cl | CH₃ | CH₃ | OCH₃ | H | O | oil |
| 120 | Cl | 6-Cl | CH₃ | CH₃ | OCH₃ | H | O | 126 |
| 121 | F | 6-F | CH₃ | CH₃ | OCH₃ | H | O | 84 |
| 122 | Cl | 5-Cl | CH₃ | CH₃ | OCH₃ | H | oil |  |

TABLE I-continued

| Comp No. | R¹ | R² | R³ | R⁴ | R⁵ | R⁶ | Y | Mp °C. |
|---|---|---|---|---|---|---|---|---|
| 123 | Cl | 6-Cl | H | OCH₃ | CH₃ | CH₃ | 6-OCH₃ | O | 115 |
| 124 | I | H | H | CH₃ | OCH₃ | 2-OCH₃ | O | oil |
| 125 | Br | H | H | CH₃ | OCH₃ | H | O | 34 |
| 126 | Cl | 6-Cl | H | CH₃ | On-C₆H₁₃ | H | O | oil |
| 127 | Cl | 6-Cl | H | CH₃ | OCH₃ | 2On-C₃H₇ | O | 46 |
| 128 | Cl | 6-Cl | H | CH₃ | OCH₃ | 2On-C₇H₁₅ | O | oil |
| 129 | Cl | 6-Cl | H | CH₃ | OCH₃ | 2On-C₁₀H₂₁ | O | oil |
| 130 | Cl | 6-Cl | H | CH₃ | OCH₃ | 2-OC(O)—CH₃ | oil |
| 131 | Cl | 6-Cl | H | CH₃ | OCH₃ | 2On-C₅H₁₁ | O | 164 |
| 132 | Cl | 6-Cl | H | CH₃ | OCH₃ | 2O(CH₂)₂—CH—(CH₃)₂ | O | oil |
| 133 | Cl | 6-Cl | H | CH₃ | OCH₃ | 2OCH₂—CH═CH₂ | O | 101 |
| 134 | Cl | 6-Cl | H | CH₃ | OCH₃ | 2OCH₂C≡CH | O | 73 |
| | | | | | | | | 123 |
| 135 | Cl | 6-Cl | H | CH₃ | OCH₃ | 2O-c-C₅H₉ | O | 89 |
| 136 | Cl | 6-Cl | H | CH₃ | OCH₃ | 6OCH₂—C₆H₅ | O | 80 |
| 137 | Cl | 6-Cl | H | CH₃ | OCH₃ | 2On-C₁₂H₂₅ | O | oil |
| 138 | Cl | 6-Cl | H | CH₃ | OCH₃ | 2OCH₂-c-C₆H₁₁ | O | 88 |
| 139 | Cl | 6-Cl | H | CH₃ | OCH₃ | 2On-C₆H₁₃ | O | oil |
| 140 | Cl | 6-Cl | H | CH₃ | On-C₁₂H₂₅ | H | O | oil |
| 141 | Cl | 6-Cl | H | CH₃ | OCH₂C(O)N—(C₂H₅)₂ | H | O | 97 |
| 142 | Cl | 6-Cl | H | CH₃ | OCH₂C(O)N—H₂ | H | O | 136 |
| 143 | Cl | 6-Cl | H | CH₃ | OCH₃ | 2O(CH₂)₂—OCH₃ | O | 84 |
| 144 | Cl | 6-CL | H | CH₃ | OCH—(C₂H5)₂ | H | O | oil |
| 145 | Cl | 6-Cl | H | CH₃ | O(CH₂)₂—OH | H | O | 87 |
| 146 | Cl | 6-Cl | H | CH₃ | O(CH₂)₃—OH | H | O | 86 |
| 147 | Cl | 6-Cl | H | CH₃ | OCH₂-p-C₆H₄-CH₃ | H | O | oil |
| 148 | Cl | 6-Cl | H | CH₃ | OCH₂-p-C₆H₄—C(CH₃)₃ | H | O | 119 |
| 149 | Cl | 6-Cl | H | CH₃ | O(CH₂)₂OCH₃ | H | O | oil |
| 150 | Cl | 6-Cl | H | CH₃ | O(CH₂)₂—C(O)-morpholide | H | O | oil |
| 151 | Cl | 6-Cl | H | CH₃ | OCH₂-p-C₆H₄—OCH₃ | H | O | 163 |
| 152 | Cl | 6-Cl | H | CH₃ | O(CH₂)₃OC₆H₅ | H | O | oil |
| 153 | Cl | 6-Cl | H | CH₃ | OCH₃ | 2OCH₂C(O)-morpholide | O | oil |
| 154 | Cl | 6-Cl | H | CH₃ | OCH₃ | 2O(CH₂)₃-morpholinyl × HCl | O | 225 |
| 155 | Cl | 6-Cl | H | CH₃ | OCH₃ | 2O(CH₂)₂—N(CH₃)₂ × HCl | O | 103 |
| 156 | Cl | 6-Cl | H | CH₃ | OCH₃ | 2O(CH₂)₂—N(C₂H₅)₂ × HCl | O | 144 |
| 157 | Cl | 6-Cl | H | CH₃ | OC₂H₅ | 2-OCH₃ | O | 68 |
| 158 | Cl | 6-Cl | H | CH₃ | OCH₃ | 2O(CH₂)₃ | O | 87 |
| 159 | Cl | 6-Cl | H | CH₃ | OCH₃ | 2O(CH₂)₃-piperidy 1 × HCl | O | 70 |
| 160 | Cl | 6-Cl | H | n-C₇H₁₅ | OCH₃ | H | O | 51 |

TABLE I-continued

| Comp No. | $R^1$ | $R^2$ | $R^{2'}$ | $R^3$ | $R^4$ | $R^5$ | $R^6$ | Y | Mp °C. |
|---|---|---|---|---|---|---|---|---|---|
| 161 | Cl | 6-Cl | H | $CH_3$ | $n$-$C_3H_7$ | $OCH_3$ | H | O | 80 |
| 162 | Cl | 6-Cl | H | $CH_3$ | $n$-$C_4H_9$ | $OCH_3$ | H | O | 89 |
| 163 | $CH_3$ | 3-$CH_3$ | H | $CH_3$ | $CH_3$ | $CH(CH_3)_2$ | H | O | 96 |
| 164 | $CH_3$ | 5-$CH_3$ | H | $CH_3$ | $CH_3$ | $OCH_3$ | 6-$OCH_3$ | O | 82 |
| 165 | Cl | 6-Cl | H | $CH_3$ | $CH_3$ | $OCH_3$ | 6-$OCH_3$ | O | oil |
| 166 | Cl | 6-Cl | H | Cl | $CH_3$ | $OCH_3$ | H | O | 114 |
| 167 | Cl | 6-Cl | H | $CH_3$ | $CH_3$ | $O(CH_2)_3CO_2C_2H_5$ | H | O | oil |
| 168 | Cl | 6-Cl | H | $CH_3$ | $CH_3$ | $OCH_2C_6H_4$—$CF_3$-$p$ | H | O | 115–117 |
| 169 | Cl | 6-Cl | H | $CH_3$ | $CH_3$ | $OCH_2SiC_2H_5(CH_3)_2$ | H | O | 85 |
| 170 | Cl | 6-Cl | H | $CH_3$ | $CH_3$ | $OC(CH_3)_3$ | H | O | 102 |
| 171 | Cl | 6-Cl | H | $CH_3$ | $CH_3$ | $OCH_2CH_2OCH_2CH_2OCH$ | H | O | oil |
| 172 | Cl | 6-Cl | H | $CH_3$ | $CH_3$ | $O(CH_2)_4Br$ | H | O | oil |
| 173 | Cl | 6-Cl | H | $CH_3$ | $CH_3$ | $OCH_3$ | 6-O$(CH_2)_3$N—$(C_2H_5)_2$ | O | oil |
| 174 | Cl | 6-Cl | H | $CH_3$ | $CH_3$ | $OCH_3$ | 6-OCH—$(CH_3)_2$ | O | 108 |
| 175 | Cl | 6-Cl | H | $CH_3$ | $CH_3$ | $OCH_3$ | 6-$OCH_2CH_2$—$OCH_2CH_2OCH_3$ | O | oil |
| 176 | Cl | 6-Cl | H | $CH_3$ | $CH_3$ | $OCOC_6H_3C_2$-2,6 | 6-$OCH_3$ | O | 186–189 |
| 177 | Cl | 6-Cl | H | $CH_3$ | CH | $OCH_3$ | 6-$OCH_3$ | O | 97 |
| 178 | Cl | 6-Cl | H | H | $CH_3$ | $CH_3$ | 6-$OCH_3$ | O | 106 |
| 179 | Cl | 6-Cl | H | $OCH_3$ | $CH_3$ | $OCH_3$ | H | O | 121–123 |
| 180 | Cl | 6-Cl | H | $CH_3$ | $CH_3$ | $NHCOCH_3$ | H | O | 155 |
| 181 | Cl | 6-Cl | H | $CH_3$ | $CH_3$ | OH | 6-OH | O | 182 |
| 182 | $CF_3$ | H | H | $CH_3$ | $CH_3$ | $OCH_3$ | 6-$OCH_3$ | O | oil |
| 183 | $CF_3$ | H | H | $CH_3$ | $CH_3$ | $OCH_3$ | H | O | oil |
| 184 | Cl | 6-Cl | H | $CH(CH_3)_2$ | $CH_3$ | $OC_4H_9$-$n$ | 6-$OC_4H_9$-$n$ | O | oil |
| 185 | Cl | 6-Cl | H | $CH_3$ | $CH_3$ | $CH_3$ | H | O | 110 |
| 186 | Cl | 6-Cl | H | $CH_3$ | H | $NO_2$ | H | O | 170 |
| 195 | | O—$CF^2$—O | | $CH_3$ | $CH_3$ | $OCH_3$ | H | O | |

EXAMPLE 4

2'-n-Butoxy-2,6-dichloro-3',4'-dimethoxy-6'-methylbenzophenone (Compound 187)
($R^1$=Cl, $R^2$=6-Cl, $R^3$=$CH_3$, $R^4$=$CH_3$, $R^5$=$OCH_3$, $R^6$=2-O-$(CH_2)_3$-$CH_3$, X=O, Y=O, m=1, n=1)

a) 2.6-Dichloro-3',4'-dimethoxy-2'-hydroxy-6'-methylbenzothenone (Compound 59)

Aluminum chloride (14.67 g, 0.1 mol), 2,6-dichlorobenzoyl chloride (20.95 g, 0.1 mol) and a solution of 3,4,5-trimethoxytoluene (18.22 g, 0.1 mol) in dichloromethane (50 ml), are slowly and consecutively added to dichloromethane stirred at 0° C., stirred for 1 h at ice bath temperatures and for 16 h at room temperature, and poured into ice. The organic layer is separated, washed with dilute hydrochloric acid and water, dried, and, after addition of silica gel (100 g), concentrated in vacuo. A flash chromatography column is packed with silica gel (400 g) and the charged silica gel is layered on top of that. Elution with petrol ether/ethyl acetate (90/10, 1 l; 80/20, 1 l; 50/50, 1 l) yields 2,6-dichloro-3',4'-dimethoxy-2'-hydroxy-6'-methylbenzophenone, 10.35 g, (30% y), mp. 161° C.

b) 2 6-Dichloro-3',4'-dimethoxy-2'-hydroxy-6'-methylbenzophenone, potassium salt (Compound 188)
($R^1$=Cl, $R^2$=6-Cl, $R^3$=$CH_3$, $R^4$=$CH_3$, $R^5$=$OCH_3$, $R^6$=2-OK, X=O, Y=O, m=1, n=0)

A solution of 2,6-dichloro-3',4'-dimethoxy-2'-hydroxy-6'-methyl-benzophenone (10.24 g, 30 mmol) is dissolved in ethanolic potassium hydroxide (1.98 g, 30 mmol; 85% in ethanol (100 ml)) and stirred at 70° C. for 15 min. The solvent is then evaporated in vacuo. The residue is dissolved in hot ethanol (50 ml), toluene is added and the solvent is evaporated in vacuo giving Compound 188, 11.7 g.

c) 2'-n-Butoxy-2,6-dichloro-3',4'-dimethoxy-6'-methylbenzophenone (Compound 187)

A mixture of 2,6-dichloro-3',4'-dimethoxy-2'-hydroxy-6'-methyl-benzophenone, potassium salt (1.13 g; 3 mmol), 1-bromobutane (0.69 g, 5 mmol) and dimethyl formamide (5 ml) are stirred at 100° C. for 8 h, and concentrated in vacuo. The residue is dissolved by shaking with a toluene/water mixture, after separation, the organic layer is collected washed with water and dried. After addition of silica gel (5 g), the solvent is evaporated. A flash chromatography column is packed with silica gel (25 g) and the charged silica gel is layered on top of that. Elution with petrol ether/ethyl acetate (95/5, 500 ml) gives the title compound, 0.82 g, (69% y) as colourless crystals, mp. 70° C.

EXAMPLE 5

Using essentially the same procedures described in Examples 1, 2 and 4 hereinabove and employing, if required, standard derivativatization methods, the following compounds shown in Table II are prepared

TABLE II

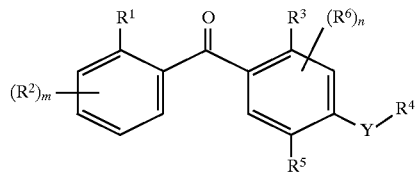

| Comp. No. | $R^1$ | $R^2$ | m | $R^3$ | Y—$R^4$ | $R^5$ | $R^6$ | n | mp °C. |
|---|---|---|---|---|---|---|---|---|---|
| 189 | $CH_3$ | 3,5,6-$CH_3$ | 3 | $CH_3$ | $OCH_3$ | $OCH_3$ | H | 0 | 103 |
| 190 | $CH_3$ | $CH_3$ | 4 | $CH_3$ | $OCH_3$ | $OCH_3$ | H | 0 | 142–144.5 |
| 191 | $CH_3$ | 3,5,6-$CH_3$ | 3 | $CH_3$ | $OCH_3$ | $OCH_3$ | 6-$OCH_3$ | 1 | 113 |
| 192 | $CH_3$ | 3,5,6-$CH_3$ | 3 | $CH_3$ | $OCH_3$ | $OCH_2CH_2CH(CH_3)_2$ | H | 0 | 73 |
| 193 | $CH_3$ | 3,5,6-$CH_3$ | 3 | $CH_3$ | $OCH_3$ | $OCH_2CH_2CH_3$ | H | 0 | 85 |
| 194 | $CH_3$ | 3,5,6-$CH_3$ | 3 | $CH_3$ | $OCH_3$ | $OCH_3$ | 6-OH | 1 | 137 |

EXAMPLE 6

2,6-Dichloro-3',4'-dimethoxybenzophenone oxime (Compound 195)
($R^1$=Cl; $R^2$=6-Cl, $R^3$=H; Y=O; $R^4$CH3; $R^5$=H, $R^6$=4-$OCH_3$; R=H A stirred dispersion of anhydrous aluminum chloride (2.93 g, 22 mmol) in methylene chloride at ice-bath temperatures is treated sequentially with a solution of 2,6-dichlorobenzonitrile oxide (3.76 g, 20 mmol) in methylene chloride and, dropwise, with a solution of veratrole (3.32 g, 24 mmol) in methylene chloride, stirred for 0.5 hour, allowed to warm to room temperature, stirred for 4–5 hours and poured into a mixture of ice and HCl. The resultant phase mixture is separated. The organic phase is washed with 2M HCl, treated with silica gel and evaporated to dryness in vacuo. The residue is placed on top of a column of silica gel and eluted with mixtures of petroleum ether and ethyl acetate (5%, 10% and 20% pet ether, respectively) to give the title product as a white solid, 1.25 g (19% y) mp 153° C.

EXAMPLE 7

2,6-Dichloro-4',5'-dimethoxy-2'-methylbenzophenone n-propyloxime (Compound 196)
$R^1$=Cl; $R^2$=6-Cl; $R^3$=$CH_3$; Y=O; $R^4$=$CH_3$; $R^5$=$OCH_3$; $R^6$=H; R=$CH_2CH_2CH_3$ A stirred solution of 2,6-dichloro-4',5'-dimethoxy-2'-methylbenzophenone oxime (1.5 g, 4.4 mmol) in anhydrous tetrahydrofuran is treated with a 60% dispersion of sodium hydride in mineral oil (0.2 g, 4.8 mmol NaH). After the cessation of hydrogen gas evolution, the reaction mixture is treated with n-propyliodide (0.82 g, 5.3 mmol), allowed to stand at room temperature for 12 hours, and diluted with water. The resultant phase mixture is extracted with ethyl acetate. The organic phases are combined and concentrated in vacuo to give a residue. The residue is chromatographed using silica gel and petroleum ether/ethyl acetate, 8/2, to give the title product as a yellow oil, 0.4 g (23.8% y) identified by NMR (67:23, E/Z isomer ratio).

EXAMPLE 8

2,6-Dichloro4',5'-dimethoxy-2'-methylbenzophenone-O-acetyloxime (Compound 197)

$R^1$=Cl; $R^2$=6-Cl; $R^3$=CH$_3$; Y=O; $R^4$=OCH$_3$; $R^5$=OCH$_3$; $R^6$=H; R=COCH$_3$

A stirred solution of 2,6-dichloro-4',5'-dimethoxy 2'-methylbenzophenone oxime (2.3 g, 6.8 mmol) in anhydrous tetrahydrofuran is treated with a 60% dispersion of sodium hydride in mineral oil (0.3 g, 7.5 mmol NaH). After the cessation of hydrogen gas evolution, the reaction mixture is treated with acetylchloride (0.55 g, 7.5 mmol) at room temperature, allowed to exotherm to 30° C., stirred at ambient temperatures for 2 hours, concentrated in vacuo, treated with water, and filtered. The filtercake is washed with water, dried and recrystallized from methanol to give the title product as white crystals, 1.0 g (38.5% y), mp 158°–149° C., identified by NMR (100% E isomer).

EXAMPLE 9

Using essentially the same procedures described for Examples 6–8 hereinabove the following compounds are obtained and shown in Table III.

TABLE III

| Compound No. | R | R3 | R6 | mp °C. |
|---|---|---|---|---|
| 198 | H | F | H | oil |
| 199 | H | H | H | 153 |
| 200 | H | CH$_3$ | H | 60–70 |
| 201 | H | CH$_3$ | 6-OCH$_3$ | 219–220 |
| 202 | CH$_3$ | CH$_3$ | H | 112–115 |
| 203 | CH(CH$_3$)$_2$ | CH$_3$ | H | 117 |
| 204 | CH$_2$CH$_2$CH$_2$CH$_3$ | CH$_3$ | H | oil |

EXAMPLE 10

2,6-Dichloro-2',3',4'-trimethoxy-6'-methyl-benzophenone

A mixture of 3,4,5-trimethoxytoluene (9.11 g; 50 mmol), octane (25 ml) and iron(III)chloride (50 mg) is stirred at 105° C., and percolating nitrogene 2,6-dichlorobenzoylchloride (12.04 g; 57.5 mmol) is added dropwise within 15 minutes. The mixture is kept at 105° C. and stirred for another 15 minutes. After cooling to 50° C. ethylacetate (50 ml) is added, the mixture shaken twice with 2N hydrochloric acid, once with water and dried. The ethylacetate is evaporated (70° C.) and the liquid cooled with stirring. At 50° C. petrolether (50 ml) is added. The white crystalls formed are sucked off, washed with petrolether and dried. Yield 12.55 g (70.7%), mp. 92° C.

EXAMPLE 11

2,6-Dichloro-2',3'-dihydroxy-4'-methoxy-6'-methyl-benzophenone

A mixture of 2,6-dichloro-2',3',4'-trimethoxy-6'-methyl-benzophenone (1.78 g; 5 mmol) hydrobromic acid (7.5 ml; 30% in acetic acid) and acetic acid (7.5 ml) is stirred at 75° C. for 2 hours. Water is added and the mixture extracted with methylenechloride. The extract is washed with water and shaken with 2N sodium hydroxide. The alcaline solution is acidified with hydrochloric acid, the separated compound dissolved in methylenechloride and the solution washed with water. After evaporation of the solvent purification is carried out by chromatography (flash column, filled with 36 g of silicagel; elution with 500 ml of petrolether/ethylacetate (4:1; v/v) and 250 ml of petrolether/ethylacetate (1:1; v/v)). the fraction containing the compound is concentrated, the compound crystallized. The yellow crystals are washed with petrolether and sucked off; 0.64 g (39% y), mp. 182° C.

EXAMPLE 12

2',3'-Di-n-butoxy-2,6-dichloro-4'-methoxy-6'-methyl-benzophenone

Sodiumhydride (0.4 g; 60%; 10 mmol) is added with stirring to a solution of 2,6-dichloro-2',3'-dihydroxy-4'-methoxy-6'-methyl-benzophenone (1.64 g; 5 mmol) in tetrahydrofurane. The solvent is evaporated and the residue dissolved in 30 ml of dimethylformamide. 1-iodo-n-butane (4.6 g; 25 mmol) is added, the mixture is stirred at 100° C. for 8 hours and then the solvent is evaporated. The residue is shaken with toluene/2N hydrochloric acid, the organic layer separated, washed with water and the solvent evaporated. The residue is purified by chromatography (flash column filled with 35 g of silicagel; elution with 500 ml of petrolether containing 2% of ethylacetate); yellow oil (0.7 g; 32% y).

EXAMPLE 13

7-(2,6-Dichlorobenzoyl)-10-methoxy-8-methyl-2,3,4,5-tetrahydro-1,6-benzodioxocin ($R^5$+$R^6$=—O—(CH$_2$)$_4$—O—)

A mixture of 2,6-dichlorobenzoyl-2',3'-dihydroxy-4'-methoxy-6'-methyl-benzophenone (3.27 g; 10 mmol), potassium carbonate (4 g), copper(II)oxide (50 mg), 1,4-dibromobutane (2.38 g; 11 mmol) and dimethylformamide (25 ml) is stirred at room temperature for 15 hours. Water is added and extracted twice with ethylacetate. The ethylacetate phase is washed with water, the solvent evaporated. The residue is purified by chromatography (flash column filled with silicagel, elution with petrolether/ethylacetate (8:2; v/v)). From the enriched fractions the product can be crystallized with methanol. White crystals (0.56 g; 14.7% y); mp. 103°–104° C.

EXAMPLE 14

2,6-Dichloro-3',4'-dimethoxy-6'-methyl-2'-phenylacetoxy-benzophenone 2,6-Dichloro-3'4'-dimethoxy-2'-dihydroxy-6'-methyl-benzophenone (3.41 g; 10 mmol) are added to a solution of potassium hydroxide (0.66 g; 85%) in methanol (30 ml). The methanol is evaporated, the residue is dissolved in dimethylformamide (30 ml), phenylacetylchloride (1.70 g; 11 mmol) is added and the mixture is stirred for 15 hours. Then water is added and the mixture is extracted three times with ethylacetate. After evaporation of the solvent methanol is added to the residue to give white crystals (1.95 g; 42.5% y); mp. 106° C.

EXAMPLE 15

2,6-Dichloro-5'-difluoromethoxy-4'-methoxy-2'-methyl-benzophenone

To a solution of 2,6-dichloro-5'-hydroxy-4'-methoxy-2'-methyl-benzophenone (1.0 g; 3.2 mmol) in dimethoxyethane (7 ml) a solution of sodium hydroxide (0.6 g; 15 mmol) in water (1 ml) is added. The mixture is heated to 60° C. with stirring, then a stream of chlorodifluoromethane is introduced for 20 minutes. After further stirring for 1.5 hours the solvent is evaporated. The residue is extracted with a mixture of trichloromethane and water. The organic phase is separated, dried and the solvent is evaporated. For purification, a flash column with silicagel (30 g) is used (elution with mixtures of petrolether/ethylacetate 9:1, then 8:2, then 7:3 (v/v)). The resulting compound forms white crystalls (0.6 g; 51.8% y); mp. 126°–128° C.

EXAMPLE 16

2,6-Dichloro-5'-propionyloxy-4'-methoxy-2'methyl-benzophenone

A mixture of 2,6-Dichloro-5'-hydroxy-4'-methoxy-2'-methyl-benzophenone and propionic acid anhydride (5 ml) is stirred at 100° C. for 5 hours. Toluene/water is added. The organic phase is dried and evaporated. The residue is purified by chromatography (flash column with silicagel (30 g), elution with toluene). The toluene is removed. After treatment with cyclohexane the residue forms white crystalls; 0.5 g (42.6% y); mp. 142°–145° C.

EXAMPLE 17

2,6-Dichloro-5'-tert-butoxy-4'-methoxy-2'-methyl-benzophenone

A solution of 2,6-dichloro-5'-hydroxy-4'-methoxy-2'-methyl-benzophenone (3.0 g; 9.6 mmol) in 50 ml of methylenechloride is cooled down to −70° C., trifluoromethane-sulfonic acid (0.3 ml) is added, then a stream of 2-methylpropene (5.5 g; 100 mmol) is introduced within 4 hours. Triethylamine (1.2 ml) is added, the temperature goes up to 20° C. The solution is shaken twice with diluted sodium hydroxide and the solvent is evaporated. The residue is purified chromatographically (flash column with 30 g of silicagel, elution with toluene/acetone 20:1 (v/v)). The residue is treated with petrolether to give 0.7 g of white crystalls (20% y); mp. 102° C.

EXAMPLE 18

2,6-Dichloro-4'-methoxy-2'-methyl-5'-phenoxy-benzophenone

A mixture of 2-methoxy-4-methyl-diphenylether (2.1 g; 10 mmol), 2,6-dichlorobenzoylchloride (2.5 g; 12 mmol) and iron(III)chloride are heated to 100° C. with stirring for 4 hours. After cooling down the mixture is shaken with toluene/water. The organic layer is dried and the solvent is evaporated. The residue is purified by chromatography (flash column filled with 30 g of silicagel, elution with toluene/petrolether 1:9, changing to 1:1 (v/v). The residue after evaporation crystallises when treated with diisopropylether; white crystalls (1.5 g; 39% y); mp. 113.5° C.

EXAMPLE 19

2,6-Dichloro-4'-methoxy-2'-methyl-benzophenone

A mixture of 2,6-dichlorobenzoylchloride (5.24 g; 25 mmol), 3-methylanisole (2.44 g; 20 mmol) and iron(III) chloride (20 mg) is heated to 100° C. for 45 minutes with stirring. After cooling, toluene is added, the mixture is shaken with water, the organic phase is dried and the solvent is evaporated. The reaction product is purified chromatograpically (flash column with 70 g of silicagel; elution with petrolether/toluene changing from 75:25 to 40:60 (v/v) ). After evaporation the residue from the main fraction is treated with petrolether to give white crystalls (1.33 g; 22.5% y); mp. 89° C.

EXAMPLE 20

5'-Bromo-2,6-dichloro-4'-methoxy-2'-methyl-benzophenone

A solution of bromine (0.25 ml in 3 ml of trichloromethane) is added dropwise to a stirred solution of 2,6-Dichloro-4'-methoxy-2'-methyl-benzophenone (1.5 g; 5 mmol in 5 ml of trichloromethane), followed by 15 minutes of stirring at 20° C. The mixture is shaken with water, sodium hydrogencarbonate solution and water. The organic phase is dried and evaporated. The residue is purified by chromatography (flash column filled with 30 g of silicagel, elution with petrolether/ethylacetate changing from 20:1 to 9:1, 8:2, 7:3 (v/v). After evaporation, the residue crystallises when treated with petrolether/toluene to give white crystalls (0.45 g; 24% y); mp. 159° C.

EXAMPLE 20

2,6-Dichloro-5'-nitro-4'-methoxy-2'methyl-benzophenone 2,6-Dichloro-4'-methoxy-2'-methyl-benzophenone (0.75 g; 2.5 mmol) is added to nitric acid (10 ml; 65%). The mixture is stirred at 80° C. for 1 hour. After addition of water the reaction product crystallises and is chromatographically purified (flash column filled with 30 g of silicagel, elution with toluene). White crystalls (0.35 g; 41% y); mp. 156°–160° C.

EXAMPLE 21

2,6-Dichloro-4'-hydroxy-5'-nitro-2'-methyl-benzophenone

Aluminumchloride (1.5 g; 11 mmol) is added to a solution of 2,6-dichloro-5'-nitro-4'-methoxy-2'-methyl-benzophenone (1.8 g; 5.3 mmol) in methylenechloride (6 ml). The mixture is stirred for 30 minutes at 20° C. and for 1 hour at 45° C., 5 ml conc. hydrochloric acid/ice are added. After shaking with 20 ml of methylenechloride the organic layer is treated with 2N hydrochloric acid and with water. After drying the solvent is evaporated, the residue purified by chromatography (flash column filled with 30 g of silicagel, elution with toluene). The residue from the main fraction is treated with diisopropylether to give yellow crystalls; (1.2 g; 73% y); mp. 170° C.

The compounds of Tables IV to X can be prepared analogously to the examples described hereinbefore.

TABLE IV

Compounds of formula

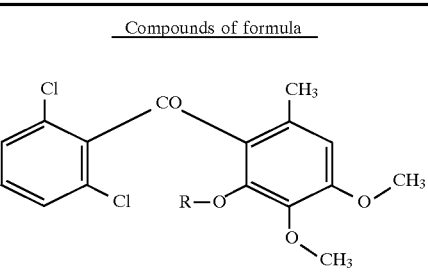

| No. | R⁵ | mp. [°C.] |
|---|---|---|
| 1 | O—C$_6$H$_5$ | 113.5 |
| 2 | Br | 159 |
| 3 | NO$_2$ | 156–60 |
| 4 | O—CH$_2$—CONH—(4-OCH$_3$—C$_6$H$_4$) | 154 |
| 5 | O—CH$_2$—CONH—C$_6$H$_5$ | 133 |
| 6 | O—CH$_2$—CONH—CH$_2$—C$_6$H$_5$ | 150 |
| 7 | O—CH$_2$—(2-pyridyl) | 114 |
| 8 | O—CH$_2$—(3-pyridyl) | 119 |
| 9 | O—CH$_2$—(4-pyridyl) | 142 |
| 10 | 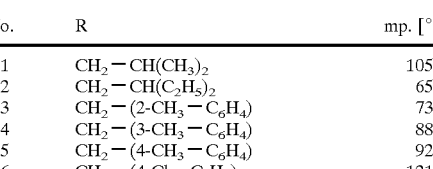 | 134 |
| 11 | O—(CH$_2$)$_4$—O—C$_6$H$_5$ | 86–9 |
| 12 | 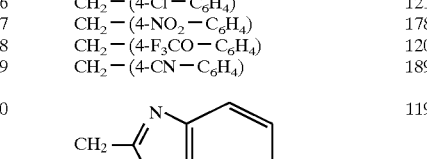 | 124 |
| 1 | O—C$_6$H$_5$ | 113.5 |
| 2 | Br | 159 |
| 3 | NO$_2$ | 156–60 |
| 4 | O—CH$_2$—CONH—(4-OCH$_3$—C$_6$H$_4$) | 154 |
| 5 | O—CH$_2$—CONH—C$_6$H$_5$ | 133 |
| 6 | O—CH$_2$—CONH—CH$_2$—C$_6$H$_5$ | 150 |
| 7 | O—CH$_2$—(2-pyridyl) | 114 |
| 8 | O—CH$_2$—(3-pyridyl) | 119 |
| 9 | O—CH$_2$—(4-pyridyl) | 142 |
| 10 | 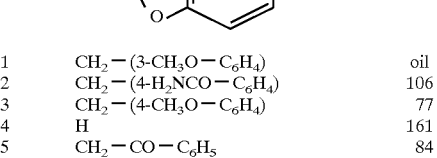 | 134 |
| 11 | O—(CH$_2$)$_4$—O—C$_6$H$_5$ | 86–9 |
| 12 | 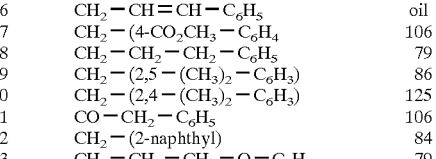 | 124 |
| 13 | 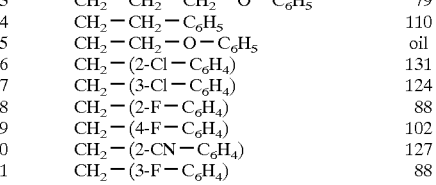 | 164 |
| 14 | O—CH$_2$—(1,4-benzodioxan) | 94 |

TABLE V

Compounds of formula (structure shown)

| No. | (R²)$_m$ | mp. [°C.] |
|---|---|---|
| 1 | 3-CH$_3$ | 82 |
| 2 | 5-CH$_3$ | oil |
| 3 | 5-CH$_3$ | 89 |
| 4 | 4,6-(CH$_3$)$_2$ | 142 |

TABLE VI

Compounds of formula (structure shown)

| No. | R | mp. [°C.] |
|---|---|---|
| 1 | CH$_2$—CH(CH$_3$)$_2$ | 105 |
| 2 | CH$_2$—CH(C$_2$H$_5$)$_2$ | 65 |
| 3 | CH$_2$—(2-CH$_3$—C$_6$H$_4$) | 73 |
| 4 | CH$_2$—(3-CH$_3$—C$_6$H$_4$) | 88 |
| 5 | CH$_2$—(4-CH$_3$—C$_6$H$_4$) | 92 |
| 6 | CH$_2$—(4-Cl—C$_6$H$_4$) | 121 |
| 7 | CH$_2$—(4-NO$_2$—C$_6$H$_4$) | 178 |
| 8 | CH$_2$—(4-F$_3$CO—C$_6$H$_4$) | 120 |
| 9 | CH$_2$—(4-CN—C$_6$H$_4$) | 189 |
| 10 | CH$_2$—(benzoxazol-2-yl) | 119 |
| 11 | CH$_2$—(3-CH$_3$O—C$_6$H$_4$) | oil |
| 12 | CH$_2$—(4-H$_2$NCO—C$_6$H$_4$) | 106 |
| 13 | CH$_2$—(4-CH$_3$O—C$_6$H$_4$) | 77 |
| 14 | H | 161 |
| 15 | CH$_2$—CO—C$_6$H$_5$ | 84 |
| 16 | CH$_2$—CH=CH—C$_6$H$_5$ | oil |
| 17 | CH$_2$—(4-CO$_2$CH$_3$—C$_6$H$_4$) | 106 |
| 18 | CH$_2$—CH$_2$—C$_6$H$_5$ | 79 |
| 19 | CH$_2$—(2,5-(CH$_3$)$_2$—C$_6$H$_3$) | 86 |
| 20 | CH$_2$—(2,4-(CH$_3$)$_2$—C$_6$H$_3$) | 125 |
| 21 | CO—CH$_2$—C$_6$H$_5$ | 106 |
| 22 | CH$_2$—(2-naphthyl) | 84 |
| 23 | CH$_2$—CH$_2$—CH$_2$—O—C$_6$H$_5$ | 79 |
| 24 | CH$_2$—CH$_2$—C$_6$H$_5$ | 110 |
| 25 | CH$_2$—CH$_2$—O—C$_6$H$_5$ | oil |
| 26 | CH$_2$—(2-Cl—C$_6$H$_4$) | 131 |
| 27 | CH$_2$—(3-Cl—C$_6$H$_4$) | 124 |
| 28 | CH$_2$—(2-F—C$_6$H$_4$) | 88 |
| 29 | CH$_2$—(4-F—C$_6$H$_4$) | 102 |
| 30 | CH$_2$—(2-CN—C$_6$H$_4$) | 127 |
| 31 | CH$_2$—(3-F—C$_6$H$_4$) | 88 |

TABLE VI-continued

Compounds of formula

| No. | R | mp. [°C.] |
|---|---|---|
| 32 | $CH_2-(3\text{-pyridyl})$ | 84 |
| 33 | $CH_2-(2\text{-}NO_2-C_6H_4)$ | 140 |
| 34 | $CH(CH_3)-C_6H_5$ | 92 |
| 35 | $CH_2-(4\text{-}CF_3-C_6H_4)$ | 125 |

TABLE VII

Compounds of formula

| No | k | mp. [°C.] |
|---|---|---|
| 1 | 1 | 119 |
| 2 | 2 | 123–5 |
| 3 | 3 | 133 |
| 4 | 4 | 103 |

TABLE VIII

Compounds of formula

| No. | R | R' | mp. [°C.] |
|---|---|---|---|
| 1 | H | $n\text{-}C_7H_{15}$ | oil |
| 2 | $CH_3$ | $n\text{-}C_7H_{15}$ | oil |
| 3 | H | $CH_2-CH_2-CH(CH_3)_2$ | 63 |
| 4 | H | $CH_2-S-C_6H_5$ | |
| 5 | $CH_3$ | $CH_2-S\text{-}t\text{-}C_4H_9$ | |

TABLE IX

Compounds of formula

| No. | R | R' | mp. [°C.] |
|---|---|---|---|
| 1 | $O-CH_3$ | $n\text{-}C_5H_{11}$ | oil |
| 2 | $O-CH_2-CH_2-S-C_6H_5$ | $CH_3$ | |
| 3 | $O-CH_2-CO-C(CH_3)_3$ | $CH_3$ | |
| 4 | H | $CH_2-O-CH_2-C_6H_5$ | |
| 5 | H | $CH_2-S-CH_3$ | |
| 6 | H | $CH_2-SO_2-C_6H_5$ | |
| 7 | H | $CH_2-S-C_6H_5$ | |
| 8 | $CH_3$ | $CH_2-S\text{-}t\text{-}C_4H_9$ | |
| 9 | OH | H | 182 |
| 10 | OH | $CH_3$ | |
| 11 | $O-CH_2-O-C_6H_5$ | $CH_3$ | |

TABLE X

Compounds of formula

| No. | R | R' | mp. [°C.] |
|---|---|---|---|
| 1 | $O-CH_3$ | $n\text{-}C_5H_{11}$ | |
| 2 | $O-CH_2-CH_2-S-C_6H_5$ | $CH_3$ | |
| 3 | $O-CH_2-CO-C(CH_3)_3$ | $CH_3$ | |
| 4 | H | $CH_2-O-CH_2-C_6H_5$ | |
| 5 | H | $CH_2-S-CH_3$ | |
| 6 | H | $CH_2-SO_2-C_6H_5$ | |
| 7 | H | $CH_2-S-C_6H_5$ | |
| 8 | $O-CH_3$ | $CH_2-S-C_6H_5$ | |
| 9 | $O-CH_2-O-CH_2-C_6H_5$ | $CH_3$ | |
| 10 | $O-CH_2-O-C_6H_5$ | $CH_3$ | |
| 11 | H | OH | |

Formulations

Emulsion Concentrate
active compound 200 g/l
ethoxylated castor oil 100 g/l
tetrahydrofurfuryl alcohol 793 g/l Biological Test Results The fungicidal activity of the compositions and compounds of the invention is investigated by means of the following tests.

a) Activity Against Cereal Powdery Mildew*Etysiphe araminis* f.sp. *hordei* and f.sp. *tritici*)

This test measures the prophylactic activity of test compositions and test compounds applied as a foliar spray. Cereal seedlings (barley, cv Golden Promise; wheat, cv Kanzler) are grown to the 1 leaf stage. The plants are then sprayed with a solution of test compound in water, made up from a 5,000 ppm stock solution in acetone containing 5,000 ppm of TRITON® X 155 (a non-ionic polyoxyethylene ether surfactant). Plants are treated using an automated spray line with atomizing nozzles. The spray volume is 20 ml. One to three days after treatment, the seedlings are inoculated with powdery mildew by shaking stock culture plants with sporulating pathogen (barley—*Erysiphe graminis* f.sp. *hordei*; wheat—*Erysiphe graminis* f.sp. *tritici*) over them. Thereafter, the plants are kept for 3 h without air movement in order to allow the spores to settle on the leaves. The plants are then kept in the greenhouse until symptoms occur. Assessment is based on the percentage of diseased leaf area compared with that on control leaves.

b) Activity Against Apple Powdery Mildew *Podosphaera leucotricha*

This test measures the prophylactic activity of test compositions and test compounds, applied as a foliar spray. Apple seedlings (cv Morgenduft) are grown to the 6–7 leaf stage and then cut back to 3 leaves, taking off the oldest and youngest leaves. The plants are sprayed with a solution (20 ml) of test compound in water, made up from a 5,000 ppm stock solution in acetone containing 5,000 ppm of TRITON® X 155. The plants are treated using an automated spray line with atomizing nozzles. One to three days after treatment, the seedlings are inoculated with powdery mildew by shaking stock culture plants with sporulating pathogen over them. Thereafter, the plants are kept for 3 h without air movement. The plants are then kept in the greenhouse until symptoms occur. Assessment is based on the percentage of diseased leaf area of treated plants compared with that of control plants.

c) Activity Against Grapevine Powdery Mildew *Uncinula necator*)

This test measures the direct protectant activity of test compositions and test compounds applied as foliar spray. Cuttings of grapevine (cv Muller-Thurgau) are grown to the 6–8 leaf stage and then cut back to 4 equally sized leaves. The plants are sprayed to run-off in a spray cabinet with a solution (20 ml) of test compound in water made up from a 5,000 ppm stock solution in acetone containing 5,000 ppm of TRITON® X 155. Two days after treatment, the cuttings are inoculated with conidia of *Uncinula necator* in a special spore setting tower. The spores are blown from freshly sporulating grape leaves (*U. necator* stock culture) into the upper hole of the settling tower and are allowed to settle on the leaves for 5 min. Then the plants are kept in a phytotron at 18° C. night and 22° C. day temperature at an interval of 12 h night and 12 h day. Illumination is accomplished by fluorescent tubes at 11,200 lux. Assessment is carried out after 21 days by visual inspection and based on the percentage of the diseased leaf area of the three youngest leaves compared with that on control plants. The results of the tests are set out in Table A and B below, in which the compounds are identified by reference to the preceding Compound Nos. allocated in Examples 1 to 9 above or to their Nos. in Tables IV to X. Absence of a rating indicates that none of the tests described above was carried out. A rating 0 indicates disease as untreated control, a rating 100 indicates no disease.

Table A

| Comp. No. | *Erysiphe graminis* barley 100 ppm | *Erysiphe graminis* wheat 100 ppm | *Podosphaera leucotricha* 100 ppm | *Uncinula necator* 200 ppm |
|---|---|---|---|---|
| *1  | 100 | 100 | 96  | 84 |
| *2  | 99  | 100 | 0   | 41 |
| *3  | 0   | 0   | 0   |    |
| 4   | 95  | 100 | 41  |    |
| 5   | 94  | 99  | 41  |    |
| 6   | 99  | 100 |     |    |
| *8  | 100 | 100 | 100 | 95 |
| *9  | 0   | 70  | 95  |    |
| *10 | 85  | 100 | 44  | 88 |
| *11 | 0   | 0   | 0   |    |
| *12 | 23  | 0   | 0   |    |
| 13  | 87  | 100 |     |    |
| *14 | 0   | 36  | 0   |    |
| *15 | 99  | 73  | 0   |    |
| 16  | 100 | 94  |     |    |
| 17  | 25  | 5   | 77  |    |
| 18  | 89  | 57  | 73  |    |
| 19  | 19  | 26  | 15  |    |
| 20  | 100 | 100 | 28  |    |
| 21  | 9   | 19  | 15  |    |
| 23  | 100 | 100 | 100 |    |
| 24  | 94  | 100 | 53  |    |
| 26  | 82  | 79  | 33  |    |
| 27  | 90  | 100 | 89  |    |
| 28  | 100 | 98  |     |    |
| 29  | 99  | 93  | 97  |    |
| 31  | 99  | 100 |     |    |
| 32  | 1   | 28  | 8   |    |
| 33  | 39  | 98  |     |    |
| 34  | 0   | 0   |     |    |
| 35  | 0   | 22  | 9   |    |
| 36  | 49  | 61  |     |    |
| 37  | 70  | 37  |     |    |
| 38  | 42  | 77  |     |    |
| 39  | 28  | 85  |     |    |
| 40  | 100 | 100 |     |    |
| 41  | 49  | 99  |     |    |
| 43  | 23  | 49  |     |    |
| 44  | 89  | 38  | 10  |    |
| 46  | 100 | 100 |     |    |
| 47  | 95  | 100 |     |    |
| 48  | 84  | 90  | 100 |    |
| 50  | 4   | 6   | 94  |    |
| 51  | 51  | 25  |     |    |
| 52  | 0   | 0   |     |    |
| 53  | 100 | 100 |     |    |
| *54 | 100 | 100 |     |    |
| 56  | 109 | 100 | 11  |    |
| *57 | 99  | 100 |     |    |
| *58 | 100 | 100 |     |    |
| *59 | 0   | 1   |     |    |
| 60  | 0   | 32  |     |    |
| 62  | 100 | 100 |     |    |
| *64 | 95  | 99  | 71  | 63 |
| *66 | 0   | 0   | 0   |    |
| *67 | 43  | 0   | 0   |    |
| *68 | 0   | 0   | 0   |    |
| *69 | 0   | 28  | 0   |    |
| *71 | 99  | 32  | 10  |    |
| *72 | 55  | 72  | 0   |    |
| *73 | 99  | 94  | 26  | 33 |
| *74 | 0   | 0   | 16  |    |
| *75 | 61  | 34  | 0   |    |
| 76  | 33  | 57  |     |    |
| *77 | 41  | 99  | 90  |    |
| *78 | 0   | 85  | 0   |    |
| *79 | 0   | 0   | 0   |    |
| 80  | 76  | 100 |     |    |
| 82  | 100 | 100 |     |    |
| 84  | 0   | 0   |     |    |
| 85  | 33  | 28  |     |    |
| 86  | 0   | 17  |     |    |
| 91  | 93  | 100 |     |    |
| *93 | 0   | 17  |     |    |
| *94 | 0   | 0   |     |    |

Table A-continued

| Comp. No. | Erysiphe graminis barley 100 ppm | Erysiphe graminis wheat 100 ppm | Podosphaera leucotricha 100 ppm | Uncinula necator 200 ppm |
|---|---|---|---|---|
| *95 | 91 | 0 | | |
| *96 | 100 | 100 | 100 | |
| *97 | 100 | 100 | 100 | |
| *98 | 100 | 100 | 100 | |
| *99 | 86 | 6 | 29 | |
| *100 | 100 | 100 | 100 | |
| *101 | 100 | 100 | 87 | |
| *102 | 100 | 100 | 100 | |
| *103 | 100 | 100 | 10 | |
| *104 | 100 | 14 | 27 | |
| *105 | 100 | 100 | 100 | |
| *106 | 100 | 100 | | |
| *107 | 0 | 21 | | |
| *108 | 100 | 100 | | |
| *109 | 100 | 100 | | |
| *110 | 100 | 100 | | |
| *111 | 95 | 100 | | |
| *112 | 0 | 19 | | |
| *113 | 0 | 28 | | |
| *114 | 0 | 17 | | |
| *115 | 100 | 60 | | |
| *116 | 100 | 64 | | |
| *117 | 100 | 100 | 6 | |
| *118 | 99 | 13 | 66 | |
| *119 | 100 | 89 | 98 | |
| *120 | 100 | 89 | 46 | |
| *121 | 100 | 100 | 37 | |
| *122 | 100 | 100 | 28 | |
| *123 | 0 | 44 | 9 | |
| *124 | 100 | 100 | 89 | |
| *125 | 100 | 28 | 8 | |
| *126 | 100 | 100 | 100 | |
| *127 | 100 | 100 | 100 | |
| *128 | 100 | 100 | 100 | |
| *129 | 100 | 100 | 100 | |
| *130 | 0 | 78 | 0 | |
| *131 | 100 | 100 | 100 | |
| *132 | 100 | 100 | 100 | |
| *133 | 100 | 100 | 100 | |
| *134 | 100 | 100 | 100 | |
| *135 | 100 | 100 | 100 | |
| *136 | 100 | 100 | 100 | |
| *137 | 100 | 100 | 97 | |
| *138 | 100 | 100 | 100 | |
| *139 | 100 | 100 | 100 | |
| *140 | 100 | 100 | 100 | |
| *141 | 97 | 100 | 0 | |
| *142 | 97 | 100 | 53 | |
| *143 | 100 | 100 | 100 | |
| *144 | 100 | 100 | 100 | |
| *145 | 84 | 97 | 80 | |
| *146 | 65 | 91 | | |
| *147 | 100 | 100 | | |
| *148 | 100 | 100 | | |
| *149 | 39 | 66 | | |
| *161 | 48 | 77 | 100 | |
| *162 | 23 | 4 | 100 | |
| *163 | 97 | 90 | 7 | |
| 166 | 100 | 100 | — | |
| 167 | 100 | 97 | 20 | |
| 168 | 100 | 100 | 2 | |
| 169 | 100 | 100 | 0 | |
| 170 | 100 | 100 | 100 | |
| 171 | 97 | 100 | 0 | |
| 172 | 100 | 97 | 100 | |
| 173 | 26 | 53 | 0 | |
| 174 | 100 | 100 | 98 | |
| 175 | 100 | 100 | 100 | |
| 176 | 0 | 0 | 8 | |
| 177 | 52 | 0 | 0 | |
| 178 | 100 | 100 | 100 | |
| 180 | 95 | 19 | — | |
| 181 | 5 | 0 | 6 | |
| 182 | 100 | 93 | 0 | |
| 183 | 100 | 74 | 0 | |
| 184 | 100 | 100 | 100 | |
| 185 | 0 | 0 | 0 | |
| 186 | 0 | 100 | 100 | |
| 189 | 100 | 100 | 100 | |
| 190 | 98 | 8 | 68 | |
| 191 | 100 | 100 | 99 | |
| 196 | 0 | 82 | 87 | |
| 197 | 71 | 78 | 1 | |
| 199 | 0 | 0 | — | |
| 200 | 100 | 100 | 41 | |
| 201 | 98 | 0 | — | |
| 202 | 0 | 92 | 92 | |

*indicates the infection with Erysiphe graminis and Podosphaera leucotricha was carried out 72 h after treatment

TABLE B

| Compound Table/No. | Erisyphe graminis barley 100 ppm | Erisyphe graminis wheat 100 ppm | Podosphaera leucotricha 100 ppm |
|---|---|---|---|
| IV/1 | 100 | 100 | — |
| 2 | 100 | 100 | 0 |
| 3 | 100 | 100 | 48 |
| 4 | 51 | 100 | 5 |
| 5 | 11 | 25 | — |
| 6 | 26 | 23 | — |
| 7 | 100 | 100 | — |
| 8 | 95 | 92 | — |
| 9 | 98 | 100 | — |
| 10 | 100 | 100 | 0 |
| 11 | 100 | 100 | 6 |
| 12 | 96 | 100 | 0 |
| 13 | 100 | 90 | 0 |
| V/1 | 100 | 100 | 97 |
| 2 | 100 | 99 | 63 |
| 3 | 100 | 100 | 25 |
| 4 | 100 | 100 | 0 |
| VI/1 | 100 | 100 | 100 |
| 2 | 100 | 100 | 100 |
| 3 | 100 | 100 | 100 |
| 4 | 100 | 100 | 100 |
| 5 | 100 | 100 | 100 |
| 6 | 100 | 100 | 100 |
| 7 | 100 | 45 | 0 |
| 8 | 100 | 100 | 100 |
| 9 | 74 | 23 | 6 |
| 10 | 100 | 100 | 96 |
| 11 | 100 | 100 | 100 |
| 12 | 100 | 0 | 0 |
| VI/13 | 100 | 100 | 100 |
| 16 | 100 | 100 | 100 |
| 17 | 100 | 58 | 100 |
| 18 | 100 | 97 | 100 |
| 19 | 100 | 100 | 100 |
| 20 | 100 | 100 | 100 |
| 21 | 100 | 100 | 38 |
| 22 | 100 | 100 | 100 |
| 23 | 100 | 95 | 19 |
| 25 | 100 | 100 | 100 |
| VII/3 | 100 | 100 | 93 |
| 4 | 100 | 100 | 100 |
| IX/1 | 100 | 100 | 100 |

What is claimed is:

1. A compound of formula Ia

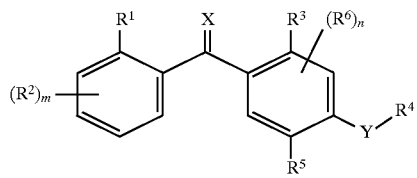

wherein
- $R^1$ represents an alkyl group;
- m is an integer of 1, 2, or 4;
- $R^2$ independently represents a halogen atom or an alkyl or alkoxy group;
- $R^3$ represents an alkyl or alkenyl group;
- $R^4$ represents an alkyl group;
- $R^5$ represents an alkoxy, alkenyloxy, alkynyloxy, alkylthio or cycloalkyloxy group;
- n is an integer of 1 or 2;
- $R^6$ independently represents an alkoxy group being optionally substituted by phenyl or phenyl being substituted by one or more substituents selected from the group comprising halogen, alkyl, alkoxy and cyano;
- X and Y each represent an oxygen atom.

2. A compound of formula

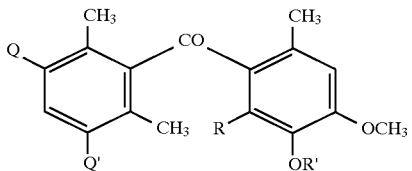

wherein Q and Q' independently represent a hydrogen atom or methyl group; R represents a hydrogen atom, a $C_3$–$C_8$-cycloalkoxy group or a, $C_1$–$C_8$-alkoxy group optionally substituted by one or more fluorine atoms, a phenyl, phenoxy, phenylthio or benzyloxy group, wherein the phenyl moiety may be substituted with one or more halogen, $C_1$–$C_4$-alkyl, $C_1$–$C_4$-alkoxy, trifluoromethyl or trifluoromethoxy groups; and R' represents hydrogen or $C_1$–$C_{10}$-alkyl optionally substituted with one or more halogen, $C_1$–$C_4$-alkoxy, phenyl, phenoxy or phenylthio groups, wherein the phenyl moiety may be substituted with one or more halogen, $C_1$–$C_4$-alkyl, $C_1$–$C_4$-alkoxy, trifluoromethyl or trifluoromethoxy groups.

* * * * *